US012076438B2

(12) United States Patent
Cobaugh et al.

(10) Patent No.: US 12,076,438 B2
(45) Date of Patent: Sep. 3, 2024

(54) COMPOSITIONS, METHODS AND USES OF MESSENGER RNA

(71) Applicant: Translate Bio, Inc., Lexington, MA (US)

(72) Inventors: Christian Cobaugh, Lexington, MA (US); Richard Wooster, Lexington, MA (US); Frank DeRosa, Lexington, MA (US); Anusha Dias, Lexington, MA (US); Shrirang Karve, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 478 days.

(21) Appl. No.: 17/066,919

(22) Filed: Oct. 9, 2020

(65) Prior Publication Data
US 2021/0106527 A1 Apr. 15, 2021

Related U.S. Application Data

(60) Provisional application No. 62/913,035, filed on Oct. 9, 2019.

(51) Int. Cl.
A61K 9/127 (2006.01)
A61K 9/00 (2006.01)
A61K 38/17 (2006.01)
A61K 38/19 (2006.01)
A61K 38/20 (2006.01)
A61K 45/06 (2006.01)
A61P 35/00 (2006.01)

(52) U.S. Cl.
CPC ............ A61K 9/127 (2013.01); A61K 9/0019 (2013.01); A61K 9/007 (2013.01); A61K 9/0078 (2013.01); A61K 38/1709 (2013.01); A61K 38/19 (2013.01); A61K 38/193 (2013.01); A61K 38/208 (2013.01); A61K 45/06 (2013.01); A61P 35/00 (2018.01)

(58) Field of Classification Search
None
See application file for complete search history.

(56) References Cited

U.S. PATENT DOCUMENTS

2015/0140070 A1* 5/2015 Heartlein ........... A61K 38/1709
514/44 R
2018/0311343 A1* 11/2018 Huang ................... A61K 39/39

FOREIGN PATENT DOCUMENTS

| WO | WO 2013/185069 A1 | 12/2013 |
| WO | WO 2015/061467 A1 | 4/2015 |
| WO | WO 2016/170176 A1 | 10/2016 |
| WO | WO 2017/201325 A1 | 11/2017 |
| WO | WO 2018/081459 A1 | 5/2018 |
| WO | WO 2018/144775 A1 | 8/2018 |
| WO | WO 2018/160540 A1 | 9/2018 |
| WO | WO 2018/213731 A1 | 11/2018 |
| WO | WO 2019/183578 A1 | 9/2019 |
| WO | WO 2019/207060 A1 | 10/2019 |
| WO | WO 2020/102172 A2 | 5/2020 |

OTHER PUBLICATIONS

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, 3(5), (2016).
Chang et al., "Combined GM-CSF and IL-12 gene therapy synergistically suppresses the growth of orthotopic liver tumors," HEPATOLOGY, vol. 45, No. 3, Mar. 1, 2007 (Mar. 1, 2007), pp. 746-754, XP055722123, ISSN: 0270-9139.
Fenton et al., "Bioinspired Alkenyl Amino Alcohol Ionizable Lipid Materials for Highly Potent In Vivo mRNA Delivery" Advanced Materials, vol. 28, No. 15, Apr. 1, 2016 (Apr. 1, 2016), pp. 2939-2943, XP055679419, ISSN: 0935-9648.
International Search Report/Written Opinion, issued by the European Patent Office Jan. 18, 2021, in corresponding PCT/US2020/054952, filed Oct. 9, 2020.
Kowalski et al., "Delivering the Messenger: Advances in Technologies for Therapeutic mRNA Delivery," Molecular Therapy, vol. 27, No. 4, Apr. 1, 2019 (Apr. 1, 2019), pp. 710-728, XP055634628, ISSN: 1525-0016.
Lai et al., "Lipid nanoparticles that deliver IL-12 messenger RNA suppress tumorigenesis in MYC oncogene-driven hepatocellular carcinoma", Journal for Immunotherapy of Cancer, Biomed Central Ltd, London, UK, vol. 6, No. 1, Nov. 20, 2018 (Nov. 20, 2018), pp. 1-11, XP021262851.
Written Opinion of the International Searching Authority dated Oct. 9, 2020 for PCT/US2020/054952.

* cited by examiner

Primary Examiner — Celeste A Roney
(74) Attorney, Agent, or Firm — LATHROP GPM LLP; James H. Velema, Esq.

(57) ABSTRACT

The present invention provides, among other things, methods and compositions for cancer treatment. The methods and compositions disclosed herein are particularly effective in reducing the size/volume of a tumor and inhibiting tumor growth.

18 Claims, 16 Drawing Sheets

| Group A (Saline; Negative Control) Tumor Volume | | | | | | | |
|---|---|---|---|---|---|---|---|
| | Study Day | | | | | | |
| Mouse # | 1 | 4 | 8 | 11 | 15 | 18 | 22 |
| 1 | 61.86 | 183.87 | 834.01 | 1506.05 | 3202.99 | | |
| 2 | 63.82 | 140.47 | 595.70 | 1115.60 | 3235.12 | | |
| 3 | 68.22 | 113.56 | 167.21 | 260.56 | 545.90 | 822.29 | 1315.92 |
| 4 | 73.75 | 188.57 | 373.79 | 601.79 | 1405.16 | 2659.10 | 3773.03 |
| 5 | 74.00 | 156.52 | 600.80 | 1079.65 | 2444.43 | 2906.31 | 6026.12 |
| 6 | 71.30 | 108.64 | 469.85 | 627.38 | 1401.70 | 1778.14 | 3931.31 |
| 7 | 62.60 | 109.39 | 255.72 | 545.84 | 1087.02 | 1683.22 | 2660.82 |
| 8 | 66.02 | 85.20 | 172.75 | 311.36 | 485.06 | 789.07 | 1799.20 |
| 9 | 56.90 | 130.89 | 317.48 | 377.30 | 1012.37 | 1287.74 | 2679.10 |
| 10 | 89.15 | 281.85 | 695.94 | 1100.24 | 2020.96 | 2791.29 | 5037.08 |
| Mean | 68.76 | 149.90 | 448.33 | 752.58 | 1684.07 | 1839.65 | 3405.32 |
| StdDev | 9.03 | 57.16 | 228.58 | 419.80 | 1005.69 | 860.77 | 1600.92 |

FIG. 5A

| | Group B (IL-12) Tumor Volume |
|---|---|
| | Study Day |

| Mouse # | 1 | 4 | 8 | 11 | 15 | 18 | 22 | 25 | 29 | 32 | 36 | 39 | 43 | 46 |
|---|---|---|---|---|---|---|---|---|---|---|---|---|---|---|
| 1 | 70.03 | 136.37 | 190.16 | 196.70 | 207.54 | 251.16 | 258.13 | 259.81 | 260.81 | 186.49 | 94.65 | 29.45 | 21.29 | 11.65 |
| 2 | 66.17 | 163.52 | 196.87 | 217.43 | 224.18 | 247.18 | 254.03 | 255.53 | 273.61 | 277.19 | 223.80 | 118.45 | 44.31 | 39.87 |
| 3 | 61.68 | 118.36 | 199.66 | 212.88 | 230.05 | 257.18 | 277.24 | 295.91 | 208.04 | 302.04 | 166.13 | 100.33 | 90.93 | 89.43 |
| 4 | 71.02 | 128.21 | 172.68 | 178.92 | 192.62 | 187.19 | 191.30 | 214.19 | 215.44 | 221.82 | 185.67 | 162.19 | 71.19 | 36.11 |
| 5 | 69.11 | 147.70 | 171.90 | 182.62 | 226.07 | 240.54 | 311.23 | 325.04 | 332.29 | 333.76 | 279.88 | 162.24 | 97.04 | 94.70 |
| 6 | 76.56 | 140.09 | 174.36 | 182.73 | 192.15 | 207.47 | 218.19 | 225.81 | 247.77 | 249.26 | 251.17 | 196.47 | 122.84 | 30.70 |
| 7 | 56.99 | 146.63 | 267.11 | 206.64 | 305.46 | 341.09 | 346.20 | 362.17 | 368.30 | 369.19 | 370.77 | 239.81 | 208.91 | 407.79 |
| 8 | 79.49 | 124.68 | 185.51 | 194.56 | 320.27 | 323.52 | 337.39 | 340.70 | 344.55 | 349.83 | 283.19 | 105.17 | 46.70 | 32.16 |
| 9 | 63.39 | 102.57 | 235.98 | 241.49 | 254.36 | 274.59 | 283.31 | 291.79 | 335.21 | 340.04 | 342.05 | 150.77 | 70.10 | 42.95 |
| 10 | 72.21 | 224.70 | 236.58 | 243.59 | 259.04 | 270.50 | 304.93 | 312.02 | 323.62 | 327.86 | 332.66 | 160.79 | 64.95 | 21.62 |
| Mean | 68.72 | 146.28 | 203.08 | 214.76 | 240.17 | 260.04 | 278.20 | 288.30 | 299.96 | 295.75 | 253.02 | 142.56 | 83.62 | 80.70 |
| StdDev | 6.78 | 33.95 | 32.58 | 37.03 | 45.31 | 46.70 | 49.57 | 48.84 | 49.00 | 60.28 | 86.77 | 57.82 | 52.65 | 118.07 |

FIG. 5B

| | | Group C (IL-2) Tumor Volume | | | | | | | | | | | |
|---|---|---|---|---|---|---|---|---|---|---|---|---|---|
| | | Study Day | | | | | | | | | | | |
| Mouse # | 1 | 4 | 8 | 11 | 15 | 18 | 22 | 25 | 29 | 32 | 36 | 39 | 43 | 46 |
| 1 | 64.11 | 190.33 | 284.66 | 315.74 | 357.14 | 451.13 | 492.85 | 585.96 | 1033.35 | 1232.77 | 1406.59 | 2151.33 | 2508.48 | 3294.45 |
| 2 | 81.90 | 226.62 | 287.83 | 312.63 | 378.79 | 448.73 | 591.12 | 643.11 | 752.98 | 833.90 | 864.50 | 1054.88 | 1383.02 | 1945.94 |
| 3 | 57.05 | 242.28 | 255.08 | 290.66 | 297.51 | 326.93 | 371.16 | 384.75 | 420.90 | 449.99 | 494.72 | 628.45 | 1435.17 | 2394.28 |
| 4 | 61.51 | 264.44 | 314.86 | 372.03 | 391.71 | 404.93 | 413.45 | 416.67 | 427.27 | 430.16 | 457.02 | 516.46 | 675.07 | 871.60 |
| 5 | 72.07 | 206.46 | 236.65 | 276.07 | 319.83 | 321.79 | 336.49 | 346.05 | 348.44 | 245.94 | 126.01 | 45.25 | 70.24 | 151.28 |
| 6 | 75.12 | 137.11 | 228.26 | 280.36 | 301.01 | 325.31 | 336.22 | 347.53 | 353.83 | 221.13 | 182.18 | 134.68 | 100.27 | 65.82 |
| 7 | 67.84 | 80.63 | 148.35 | 262.11 | 308.80 | 317.94 | 377.62 | 404.51 | 448.55 | 458.55 | 474.64 | 489.19 | 501.85 | 869.24 |
| 8 | 72.08 | 153.63 | 213.60 | 222.86 | 243.76 | 259.53 | 262.05 | 276.24 | 283.40 | 307.30 | 367.47 | 841.14 | 1563.60 | 2280.54 |
| 9 | 67.96 | 112.40 | 144.65 | 180.65 | 223.99 | 231.46 | 244.66 | 253.81 | 263.17 | 263.46 | 293.74 | 312.19 | 335.03 | 341.80 |
| 10 | 67.54 | 260.39 | 461.32 | 526.73 | 598.77 | 795.68 | 857.24 | 1180.38 | 2105.09 | 2449.94 | 3331.21 | | | |
| Mean | 68.72 | 187.03 | 257.51 | 304.03 | 342.13 | 388.33 | 428.29 | 484.10 | 643.20 | 689.31 | 860.21 | 663.73 | 962.53 | 1332.76 |
| StdDev | 7.07 | 64.15 | 90.88 | 93.98 | 104.78 | 160.57 | 162.27 | 274.46 | 566.04 | 694.17 | 964.30 | 633.04 | 819.97 | 1164.47 |

FIG. 5C

| Mouse # | \multicolumn{14}{c}{Group D (STING/IL-12) Tumor Volume} |
|---|---|---|---|---|---|---|---|---|---|---|---|---|---|---|
| | \multicolumn{14}{c}{Study Day} |
| | 1 | 4 | 8 | 11 | 15 | 18 | 22 | 25 | 29 | 32 | 36 | 39 | 43 | 46 |
| 1 | 74.06 | 120.97 | 131.67 | 142.33 | 164.52 | 169.64 | 177.38 | 237.27 | 239.61 | 289.25 | 233.68 | 174.55 | 100.67 | 59.50 |
| 2 | 65.28 | 170.84 | 207.39 | 235.71 | 254.08 | 258.91 | 266.92 | 280.01 | 283.83 | 300.66 | 317.30 | 325.94 | 204.44 | 80.22 |
| 3 | 71.00 | 120.12 | 178.13 | 186.84 | 212.17 | 258.10 | 266.11 | 285.66 | 297.10 | 261.28 | 131.15 | 114.40 | 102.06 | 36.51 |
| 4 | 57.78 | 130.89 | 153.41 | 182.69 | 217.81 | 229.54 | 245.54 | 251.46 | 258.56 | 208.61 | 175.35 | 139.03 | 83.40 | 66.03 |
| 5 | 92.81 | 229.84 | 289.21 | 323.60 | 341.54 | 348.94 | 357.24 | 379.45 | 390.71 | 325.74 | 222.18 | 205.66 | 75.30 | 58.84 |
| 6 | 63.32 | 186.52 | 312.91 | 333.62 | 354.00 | 369.25 | 382.21 | 387.48 | 391.78 | 303.85 | 217.35 | 107.41 | 78.69 | 47.60 |
| 7 | 60.98 | 128.96 | 157.98 | 198.12 | 210.23 | 218.12 | 223.96 | 236.84 | 241.20 | 243.49 | 142.54 | 123.84 | 75.63 | 30.80 |
| 8 | 73.82 | 175.48 | 193.09 | 211.92 | 221.52 | 250.59 | 265.70 | 324.15 | 354.84 | 364.38 | 263.06 | 141.29 | 118.28 | 48.24 |
| 9 | 65.16 | 140.67 | 181.98 | 230.38 | 265.04 | 302.72 | 308.70 | 318.74 | 331.46 | 507.75 | 1151.66 | 212.23 | | |
| 10 | 63.84 | 133.72 | 167.19 | 184.60 | 196.56 | 204.04 | 212.73 | 220.68 | 225.11 | 227.77 | 229.22 | 236.24 | 239.27 | 246.49 |
| Mean | 68.80 | 153.80 | 197.30 | 222.88 | 243.75 | 260.99 | 270.65 | 292.17 | 301.42 | 313.28 | 311.35 | 368.06 | 119.75 | 75.13 |
| StdDev | 9.98 | 35.81 | 58.90 | 61.74 | 61.53 | 63.01 | 63.52 | 59.13 | 62.65 | 90.23 | 310.70 | 616.52 | 60.28 | 66.04 |

FIG. 5D

| Mouse # | \multicolumn{14}{c}{Group E (STING/IL-12/GM-CSF) Tumor Volume} |
|---|---|---|---|---|---|---|---|---|---|---|---|---|---|---|

| Mouse # | 1 | 4 | 8 | 11 | 15 | 18 | 22 | 25 | 29 | 32 | 36 | 39 | 43 | 46 |
|---|---|---|---|---|---|---|---|---|---|---|---|---|---|---|
| 1 | 69.89 | 208.42 | 248.13 | 268.89 | 281.54 | 286.35 | 290.46 | 296.27 | 302.81 | 304.69 | 175.98 | 118.58 | 27.39 | 13.93 |
| 2 | 72.36 | 183.49 | 217.43 | 232.98 | 246.33 | 250.66 | 255.19 | 259.70 | 272.03 | 273.88 | 166.77 | 95.38 | 55.53 | 8.80 |
| 3 | 70.13 | 180.67 | 203.35 | 245.75 | 250.63 | 264.07 | 285.41 | 297.11 | 304.97 | 311.31 | 224.01 | 118.42 | 49.63 | 30.56 |
| 4 | 80.93 | 135.43 | 142.51 | 176.98 | 208.85 | 278.58 | 321.18 | 337.78 | 340.35 | 353.20 | 513.10 | 702.01 | 1499.48 |  |
| 5 | 78.47 | 231.91 | 300.31 | 328.72 | 353.24 | 373.62 | 375.04 | 381.83 | 384.52 | 389.06 | 264.54 | 98.05 | 46.69 | 25.09 |
| 6 | 69.11 | 167.57 | 230.40 | 251.52 | 259.60 | 276.98 | 278.66 | 284.23 | 291.45 | 294.14 | 176.40 |  |  |  |
| 7 | 77.24 | 133.81 | 195.35 | 196.26 | 201.93 | 205.77 | 211.11 | 222.50 | 233.05 | 237.46 | 116.36 | 90.22 | 46.01 | 26.71 |
| 8 | 67.21 | 170.98 | 187.02 | 212.92 | 261.27 | 276.06 | 277.91 | 288.28 | 315.55 | 317.16 | 191.23 | 118.41 | 87.84 | 41.56 |
| 9 | 64.52 | 189.23 | 239.78 | 251.03 | 264.09 | 272.20 | 281.16 | 286.30 | 295.38 | 302.77 | 215.92 | 124.40 | 47.17 | 42.26 |
| 10 | 67.56 | 169.18 | 190.80 | 239.67 | 274.67 | 286.23 | 307.08 | 315.57 | 319.22 | 344.99 | 237.06 | 156.36 | 58.22 | 31.44 |
| Mean | 68.74 | 177.07 | 214.51 | 239.47 | 260.22 | 277.24 | 288.31 | 296.94 | 305.93 | 312.87 | 228.34 | 180.43 | 213.11 | 26.18 |
| StdDev | 6.31 | 29.79 | 43.29 | 41.07 | 41.71 | 41.52 | 42.53 | 42.81 | 40.03 | 42.44 | 108.19 | 196.64 | 482.65 | 11.10 |

FIG. 5E

| Group F (STING/IL-12/FLT-3L/GM-CSF) Tumor Volume | | | | | | | | | | | | | | |
|---|---|---|---|---|---|---|---|---|---|---|---|---|---|---|
| | | | | | | | Study Day | | | | | | | |
| Mouse # | 1 | 4 | 8 | 11 | 15 | 18 | 22 | 25 | 29 | 32 | 36 | 39 | 43 | 46 |
| 1 | 67.01 | 162.80 | 185.74 | 200.65 | 234.93 | 269.48 | 311.72 | 336.23 | 353.23 | 360.32 | 210.48 | 184.42 | 75.06 | 35.91 |
| 2 | 66.59 | 111.81 | 139.78 | 157.27 | 198.72 | 207.80 | 307.19 | 343.53 | 356.92 | 304.78 | 231.72 | 206.89 | 175.43 | 112.90 |
| 3 | 60.02 | 174.01 | 240.23 | 281.27 | 295.98 | 306.86 | 314.27 | 324.89 | 328.27 | 330.82 | 112.01 | 66.25 | 38.20 | 33.20 |
| 4 | 79.60 | 192.78 | 217.81 | 233.27 | 243.26 | 266.15 | 272.53 | 291.02 | 305.93 | 309.00 | 144.28 | 113.35 | 89.54 | 46.40 |
| 5 | 74.36 | 93.27 | 119.71 | 177.25 | 187.28 | 211.52 | 249.07 | 275.00 | 299.76 | 339.35 | 235.84 | 189.60 | 81.14 | 51.39 |
| 6 | 69.84 | 126.10 | 132.17 | 165.01 | 186.81 | 196.15 | 207.49 | 256.39 | 259.41 | 267.96 | 144.83 | 128.07 | 65.14 | 43.49 |
| 7 | 73.47 | 158.17 | 274.49 | 269.50 | 310.69 | 355.27 | 306.37 | 376.08 | 377.15 | 382.89 | 172.56 | 108.69 | 67.99 | 18.73 |
| 8 | 63.72 | 111.34 | 143.34 | 205.75 | 211.90 | 223.30 | 244.53 | 264.90 | 274.08 | 278.20 | 231.66 | 195.25 | 61.67 | 47.31 |
| 9 | 67.19 | 130.65 | 202.14 | 228.89 | 234.18 | 256.00 | 259.87 | 262.52 | 322.66 | 307.51 | 233.27 | 233.42 | 465.34 | 909.62 |
| 10 | 64.35 | 130.93 | 212.75 | 234.44 | 243.13 | 254.06 | 266.61 | 279.63 | 318.74 | 323.65 | 167.63 | 136.90 | 132.14 | 131.52 |
| Mean | 68.72 | 145.19 | 186.82 | 217.33 | 234.69 | 254.63 | 280.27 | 301.04 | 320.11 | 329.47 | 186.95 | 156.69 | 124.22 | 143.05 |
| StdDev | 5.77 | 35.22 | 51.64 | 45.14 | 42.21 | 49.03 | 45.24 | 41.22 | 37.35 | 39.63 | 46.37 | 52.59 | 126.54 | 271.72 |

FIG. 5F

| | \multicolumn{14}{c|}{Group G (STING/IL-12/NLRP3/GM-CSF) Tumor Volume} |
|---|---|---|---|---|---|---|---|---|---|---|---|---|---|
| | \multicolumn{14}{c|}{Study Day} |
| Mouse # | 1 | 4 | 8 | 11 | 15 | 18 | 22 | 25 | 29 | 32 | 36 | 39 | 43 | 46 |
| 1 | 69.27 | 120.85 | 168.09 | 203.61 | 236.28 | 250.05 | 257.80 | 286.49 | 299.73 | 312.72 | 317.05 | 366.74 | | |
| 2 | 64.96 | 173.21 | 225.42 | 236.95 | 252.82 | 258.21 | 274.77 | 290.70 | 294.08 | 302.20 | 128.90 | 111.90 | 57.49 | 29.62 |
| 3 | 70.24 | 147.46 | 197.45 | 236.11 | 248.30 | 272.47 | 303.84 | 310.47 | 314.67 | 198.87 | 103.11 | 64.73 | 54.34 | 26.99 |
| 4 | 95.85 | 152.26 | 173.13 | 252.31 | 270.16 | 283.30 | 296.76 | 317.04 | 323.00 | 339.69 | 196.75 | 172.01 | 92.73 | 39.63 |
| 5 | 59.31 | 167.12 | 202.58 | 276.68 | 284.45 | 331.91 | 334.77 | 341.15 | 344.05 | 345.00 | | | | |
| 6 | 60.57 | 228.38 | 292.01 | 305.62 | 329.88 | 339.29 | 345.13 | 355.20 | 369.88 | 376.21 | 192.61 | 164.40 | 92.27 | 41.32 |
| 7 | 59.90 | 118.13 | 144.77 | 198.09 | 199.72 | 205.04 | 216.66 | 232.12 | 236.65 | 243.75 | 157.41 | 125.46 | 57.20 | 41.27 |
| 8 | 62.77 | 190.01 | 200.00 | 278.73 | 299.50 | 317.05 | 338.86 | 343.53 | 347.74 | 348.96 | 166.05 | | | |
| 9 | 73.88 | 171.84 | 234.25 | 243.49 | 254.89 | 273.41 | 290.95 | 312.02 | 320.84 | 321.87 | 173.13 | 120.54 | 84.87 | 33.66 |
| 10 | 70.70 | 138.67 | 257.06 | 294.42 | 318.16 | 323.66 | 330.87 | 342.70 | 364.49 | 369.47 | 163.14 | 157.84 | 78.28 | 31.19 |
| Mean | 68.74 | 160.79 | 209.48 | 252.60 | 270.32 | 285.44 | 299.24 | 313.14 | 321.49 | 315.87 | 183.35 | 162.95 | 73.88 | 34.82 |
| StdDev | 10.81 | 33.15 | 45.17 | 36.20 | 40.15 | 42.55 | 41.05 | 36.75 | 39.24 | 55.92 | 59.73 | 36.84 | 17.14 | 5.89 |

FIG. 5G

| | \multicolumn{14}{c|}{Group H (STING/IL-12/IL-2/GM-CSF) Tumor Volume} |
|---|---|---|---|---|---|---|---|---|---|---|---|---|---|---|
| | \multicolumn{14}{c|}{Study Day} |
| Mouse # | 1 | 4 | 8 | 11 | 15 | 18 | 22 | 25 | 29 | 32 | 36 | 39 | 43 | 46 |
| 1 | 60.51 | 111.97 | 168.01 | 197.72 | 220.74 | 230.08 | 238.23 | 259.20 | 268.56 | 272.01 | 205.27 | 96.33 | 73.09 | 45.34 |
| 2 | 60.29 | 354.39 | 364.30 | 392.33 | 409.85 | 431.30 | 434.07 | 466.62 | 470.95 | 477.10 | 310.32 | 306.28 | 550.55 | 744.58 |
| 3 | 66.88 | 189.21 | 202.58 | 215.10 | 232.63 | 256.49 | 266.06 | 279.36 | 289.63 | 293.20 | 179.07 | 96.09 | 58.91 | 0.00 |
| 4 | 71.95 | 153.18 | 224.42 | 233.73 | 245.45 | 260.94 | 278.63 | 303.56 | 315.93 | 313.68 | 295.06 | 269.45 | 255.69 | 207.01 |
| 5 | 68.03 | 153.69 | 219.95 | 227.22 | 247.97 | 264.66 | 272.69 | 283.95 | 287.08 | 288.69 | 191.10 | 119.34 | 96.30 | |
| 6 | 72.09 | 132.09 | 203.93 | 266.16 | 263.50 | 294.86 | 307.77 | 329.21 | 339.79 | 341.33 | 257.34 | 226.24 | 186.61 | 105.36 |
| 7 | 76.52 | 159.48 | 205.38 | 226.03 | 245.80 | 310.93 | 319.70 | 332.17 | 388.16 | 414.14 | 208.41 | 172.19 | 150.16 | 63.27 |
| 8 | 64.39 | 126.62 | | | | | | | | | | | | |
| 9 | 67.87 | 153.63 | 201.42 | 239.17 | 253.76 | 286.70 | 294.65 | 317.97 | 321.62 | 329.88 | 212.78 | 106.75 | 52.28 | 40.07 |
| 10 | 78.96 | 121.04 | 240.69 | 261.89 | 274.39 | 283.86 | 290.63 | 295.16 | 302.92 | 310.08 | 112.55 | 48.91 | 39.21 | 26.98 |
| Mean | 68.75 | 165.43 | 225.63 | 251.26 | 268.23 | 291.09 | 300.27 | 319.13 | 331.63 | 338.34 | 219.10 | 160.06 | 162.78 | 154.08 |
| StdDev | 6.23 | 70.07 | 55.69 | 57.16 | 56.45 | 57.73 | 55.58 | 60.34 | 62.82 | 66.30 | 60.67 | 88.57 | 162.10 | 246.93 |

FIG. 5H

| Group 1 (FFL, negative control) Tumor Volume | | | | | | | | | |
|---|---|---|---|---|---|---|---|---|---|
| | | | | Study Day | | | | | |
| Mouse # | 1 | 4 | 8 | 11 | 15 | 18 | 22 | 25 | 29 |
| 1 | 74.02 | 127.84 | 203.52 | 272.21 | 598.29 | 1163.92 | 2231.68 | 3777.19 | |
| 2 | 60.39 | 179.69 | 282.22 | 290.51 | 368.68 | 406.25 | 727.81 | 1260.79 | 2400.43 |
| 3 | 72.23 | 178.55 | 354.94 | 475.10 | 1002.86 | 1794.28 | 2281.77 | | |
| 4 | 68.33 | 105.68 | 418.83 | 592.46 | 956.21 | 1748.66 | 2376.03 | 4325.58 | |
| 5 | 78.55 | 171.01 | 281.98 | 301.73 | 345.60 | 485.74 | 781.52 | 1572.18 | 3561.89 |
| 6 | 60.41 | 138.07 | 228.61 | 269.84 | 417.28 | 616.47 | 1029.20 | 1660.45 | 3475.51 |
| 7 | 65.00 | 124.49 | 324.10 | 424.06 | 613.24 | 787.73 | 1352.63 | 2600.39 | 3968.86 |
| 8 | 62.02 | 147.69 | 310.65 | 370.08 | 544.69 | 833.21 | 1644.81 | 2775.43 | 5743.63 |
| 9 | 69.05 | 245.99 | 317.27 | 385.11 | 484.74 | 686.29 | 1147.61 | 1804.93 | |
| 10 | 77.27 | 189.33 | 294.77 | 466.31 | 831.24 | 1483.05 | 2348.47 | 3913.47 | |
| Mean | 68.73 | 160.83 | 301.69 | 384.94 | 616.28 | 1000.56 | 1592.15 | 2632.27 | 3830.06 |
| StdDev | 6.73 | 40.79 | 60.71 | 106.29 | 237.61 | 514.99 | 670.82 | 1144.27 | 1216.81 |

FIG. 5I

COMPOSITIONS, METHODS AND USES OF MESSENGER RNA

CROSS-REFERENCE TO RELATED APPLICATIONS

This application claims the benefit of, and priority to U.S. Ser. No. 62/913,035 filed on Oct. 9, 2019, the content of which is incorporated herein in its entirety.

BACKGROUND

Cancer is the most common cause of death in many parts of the world and more than 2.5 million cancer cases are diagnosed worldwide each year. Recent advances in our understanding of the molecular biology of cancer have shown that cancer is a genetic disorder that causes abnormal growth of diseased cells. Many cancer treatments exist, including surgery, chemotherapy, radiation therapy, gene therapy, and small and protein molecules. However, these treatments often function by non-specific interactions with cellular targets, produce undesirable side effects, and do not treat the root of the disease. Cancer still remains highly resistant to currently available therapies.

SUMMARY OF INVENTION

The present invention provides an improved mRNA therapeutics for the treatment for cancer. In particular, methods described herein provides an effective in vivo delivery of mRNAs encoding immune modulating proteins or peptides, useful in immune-oncology.

In one aspect, the present invention provides, among other things, a method for treating cancer, comprising administering to a subject in need thereof a composition comprising an mRNA encoding a protein or a peptide encapsulated within a lipid nanoparticle at an effective dose and an administration interval such that the size of a tumor is reduced or the growth of a tumor is inhibited.

In another aspect, the present invention provides a method of treating cancer, comprising administering to a subject in need thereof a composition comprising two or more mRNAs each encoding a protein or a peptide encapsulated within one or more lipid nanoparticles at an effective dose and an administration interval such that the size of a tumor is reduced or the growth of a tumor is inhibited, wherein at least two of the two or more mRNAs each encode a different protein or peptide from the other.

In some embodiments, the two or more mRNAs comprise a first mRNA encoding a first protein or peptide encapsulated within a first lipid nanoparticle and a second mRNA encoding a second protein or peptide encapsulated with a second lipid nanoparticle.

In some embodiments, at least one of the protein or the peptide modulates immune response. In some embodiments, at least one of the protein or the peptide is IL-12, IL-2, IL-6, IL-15, STING, MCP-3, GM-CSF, FLT-3L, NLRP3, IFN-γ, TNF-α, NLRP1, CCL5 or a combination thereof.

In some embodiments, the two of two or more mRNAs encode IL-12 and STING, respectively. In some embodiments, the two or more mRNAs comprise at least three mRNAs that encode STING, IL-12, and GM-CSF, respectively. In some embodiments, the two or more mRNAs comprise at least four mRNAs that encode STING, IL-12, FLT-3L, and GM-CSF, respectively. In some embodiments, the two or more mRNAs comprise at least four mRNAs that encode STING, IL-12, NLRP3, and GM-CSF, respectively. In some embodiments, the two or more mRNAs comprise at least four mRNAs that encode STING, IL-12, IL-2, and GM-CSF, respectively.

In some embodiments, the STING is a mutant form of the STING. In some embodiments, the mutant form allows the STING to be constitutively active.

In some embodiments, at least one of the protein or the peptide does not modulate an immune response.

In some embodiments, the method results in a percent tumor growth inhibition of greater than 50% relative to a control 7 days after administration of an initial dose. In some embodiments, method results in a percent tumor growth inhibition of greater than 60% relative to a control 10 days after administration of an initial dose. In some embodiments, method results in a percent tumor growth inhibition of greater than 70% relative to a control 10 days after administration of an initial dose. In some embodiments, method results in a percent tumor growth inhibition of greater than 80% relative to a control 10 days after administration of an initial dose. In some embodiments, the method results in a percent tumor growth inhibition of greater than 80% relative to a control 20 days after administration of an initial dose. In some embodiments, the method results in a percent tumor growth inhibition of greater than 85% relative to a control 20 days after administration of an initial dose. In some embodiments, the method results in a percent tumor growth inhibition of greater than 90% relative to a control 20 days after administration of an initial dose.

In some embodiments, the administration of the composition results in a percent change of body weight in the subject of less than 15% relative to a control. In some embodiments, the administration of the composition results in a percent change of body weight in the subject of less than 10% relative to a control. In some embodiments, the administration of the composition results in a percent change of body weight in the subject of less than 5% relative to a control.

In some embodiments, the control is a subject with the same disease status without treatment. In some embodiments, the control is a body weight of the subject prior to the administration of the composition.

In some embodiments, the lipid nanoparticle comprises one or more cationic lipids, one or more non-cationic lipids, and one or more PEG-modified lipids. In some embodiments, the lipid nanoparticle further comprises cholesterol or one or more cholesterol-based lipids.

In some embodiments, the first lipid nanoparticle comprises a first cationic lipid and the second lipid nanoparticle comprises a second cationic lipid, wherein the first cationic lipid is different from the second cationic lipid.

In some embodiments, the one or more cationic lipids are selected from the group consisting of cKK-E12, OF-02, C12-200, MC3, DLinDMA, DLinkC2DMA, ICE (Imidazol-based), HGT5000, HGT5001, HGT4003, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24), and combinations thereof. In some embodiments, the one or more cationic lipids comprise cKK-E12.

In some embodiments, the composition is administered intratumorally. In some embodiments, the composition is administered subcutaneously. In some embodiments, the composition is administered intradermally. In some embodiments, the composition is administered intravenously. In some embodiments, the composition is administered by pulmonary administration. In some embodiments, the composition is administered by nebulization.

In some embodiments, the method comprises injecting a single dose. In some embodiments, the method comprises injecting multiple doses periodically. In some embodiments, the single dose or the multiple doses range from 0.1 µg-100 mg mRNA. In some embodiments, the single dose or the multiple doses range from 0.1 µg-50 mg mRNA. In some embodiments, the single dose or the multiple doses range from 0.1 µg-25 mg mRNA. In some embodiments, the single dose or the multiple doses range from 0.1 µg-10 mg mRNA. In some embodiments, the single dose or the multiple doses range from 1-1 mg. In some embodiments, the single dose or the multiple doses range from 1-100 µg mRNA.

In some embodiments, the single dose is or the multiple doses are 0.1 µg. In some embodiments, the single dose is or the multiple doses are 0.3 µg. In some embodiments, the single dose is or the multiple doses are 0.5 µg. In some embodiments, the single dose is or the multiple doses are 1 µg. In some embodiments, the single dose is or the multiple doses are 5 µg. In some embodiments, the single dose is or the multiple doses are 10 µg. In some embodiments, the single dose is or the multiple doses are 25 µg. In some embodiments, the single dose is or the multiple doses are 50 µg. In some embodiments, the single dose is or the multiple doses are 100 µg.

In some embodiments, the single dose or the multiple doses range from 0.01 µg/kg-10 mg/kg (mRNA/body weight). In some embodiments, the single dose or the multiple doses range from 0.01 µg/kg-8 mg/kg (mRNA/body weight). In some embodiments, the single dose or the multiple doses range from 0.01 µg/kg-6 mg/kg (mRNA/body weight). In some embodiments, the single dose or the multiple doses range from 0.01 µg/kg-5 mg/kg (mRNA/body weight). In some embodiments, the single dose or the multiple doses range from 0.1 µg/kg-5 mg/kg (mRNA/body weight). In some embodiments, the single dose or the multiple doses range from 0.1 µg/kg-1 mg/kg (mRNA/body weight). In some embodiments, the single dose or the multiple doses range from 0.1 µg/kg-0.5 mg/kg (mRNA/body weight).

In some embodiments, each of the multiple doses comprise the same dosage amount of mRNA. In some embodiments, each of the multiple doses comprise a different dosage amount of mRNA.

In some embodiments, each of the multiple doses are injected 1 day to 3 weeks apart. In some embodiments, each of the multiple doses are injected daily. In some embodiments, each of the multiple doses are injected 3 days apart. In some embodiments, each of the multiple doses are injected weekly. In some embodiments, each of the multiple doses are injected 10 days apart. In some embodiments, each of the multiple doses are injected bi-weekly. In some embodiments, each of the multiple doses are injected monthly. In some embodiments, each of the multiple doses are injected bi-monthly.

In some embodiments, the mRNA comprises one or more modified nucleotides. In some embodiments, the mRNA comprises a 5' untranslated region (5' UTR) and/or a 3' untranslated region (3' UTR). In some embodiments, the mRNA comprises a 5' untranslated region (5' UTR). In some embodiments, the mRNA comprises a 3' untranslated region (3' UTR).

In some embodiments, the administration of the composition activates T cells in the subject. In some embodiments, the method further comprises administering to the subject a composition comprising a check point inhibitor. In some embodiments, the method does not comprise administering to the subject a composition comprising a check point inhibitor. In some embodiments, the check point inhibitor inhibits PD1, PD-L1, CTLA-4, B7, BTLA, HVEM, TIM-3, GAL-9, LAG3, VISTA, KIR, 2B4, CD160, CGEN-15049, CHK1, CHK2, A2aR, or a combination thereof. In some embodiments, the check point inhibitor inhibits PD1. In some embodiments, the check point inhibitor inhibits PD-L1. In some embodiments, the check point inhibitor inhibits CTLA-4. In some embodiments, the check point inhibitor inhibits B7. In some embodiments, the check point inhibitor inhibits BTLA. In some embodiments, the check point inhibitor inhibits HVEM. In some embodiments, the check point inhibitor inhibits TIM-3. In some embodiments, the check point inhibitor inhibits GAL-9. In some embodiments, the check point inhibitor inhibits LAG3. In some embodiments, the check point inhibitor inhibits VISTA. In some embodiments, the check point inhibitor inhibits KIR. In some embodiments, the check point inhibitor inhibits 2B4. In some embodiments, the check point inhibitor inhibits CD160. In some embodiments, the check point inhibitor inhibits CGEN-15049. In some embodiments, the check point inhibitor inhibits CHK1. In some embodiments, the check point inhibitor inhibits CHK2. In some embodiments, the check point inhibitor inhibits A2aR.

In some embodiments, the one or more mRNAs are encapsulated within the same lipid nanoparticle. In some embodiments, the one or more mRNAs are encapsulated within separate lipid nanoparticles.

In one aspect, the present invention provides a pharmaceutical composition for treating cancer, comprising one or more mRNAs each encoding, respectively, IL-12, IL-2, IL-6, IL-15, STING, MCP-3, GM-CSF, FLT-3L, NLRP3, IFN-γ, TNF-α, NLRP1, CCL5, or a combination thereof, wherein the one or more mRNAs are encapsulated within one or more lipid nanoparticles comprising at least one lipid nanoparticle comprising cKK-E12 as a cationic lipid.

In some embodiments, the one or more mRNAs encode IL-12 and STING. In some embodiments, the one or more mRNAs encode STING, IL-12, and GM-CSF. In some embodiments, the one or more mRNAs encode STING, IL-12, FLT-3L, and GM-CSF. In some embodiments, the one or more mRNAs encode STING, IL-12, NLRP3, and GM-CSF. In some embodiments, the one or more mRNAs encode STING, IL-12, IL-2, and GM-CSF.

In some embodiments, the composition further comprises an additional mRNA encoding a check point inhibitor. In some embodiments, the check point inhibitor inhibits PD1, PD-L1, CTLA-4, B7, BTLA, HVEM, TIM-3, GAL-9, LAG3, VISTA, KIR, 2B4, CD160, CGEN-15049, CHK1, CHK2, A2aR, or a combination thereof.

In some embodiments, the method results in an ascopal effect. In some embodiments, the method results in an abscopal effect.

In some embodiments, the method results in a percent tumor growth inhibition of an untreated tumor greater than 50% relative to a control 7 days after administration of an initial dose.

In some embodiments, the method results in a percent tumor growth inhibition of an untreated tumor greater than 60%, greater than 70%, or greater than 80% relative to a control 10 days after administration of an initial dose.

In some embodiments, the method results in a percent tumor growth inhibition of an untreated tumor greater than 80%, greater than 85%, or greater than 90% relative to a control 20 days after administration of an initial dose.

In some embodiments, the method increases survival of a subject who has cancer.

BRIEF DESCRIPTION OF FIGURES

The drawings are for illustration purposes, not for limitation.

FIG. 5 is a series of tables showing tumor volumes ($mm^3$) of individual mouse in each Group A (FIG. 5A), Group B (FIG. 5B), Group C (FIG. 5C), Group D (FIG. 5D), Group E (FIG. 5E), Group F (FIG. 5F), Group G (FIG. 5G), Group H (FIG. 5H), and Group I (FIG. 5I). Mean and standard deviation values are indicated in the last two rows. Blank space indicates death. Sample size for each group was 10.

DEFINITIONS

Figure 1:
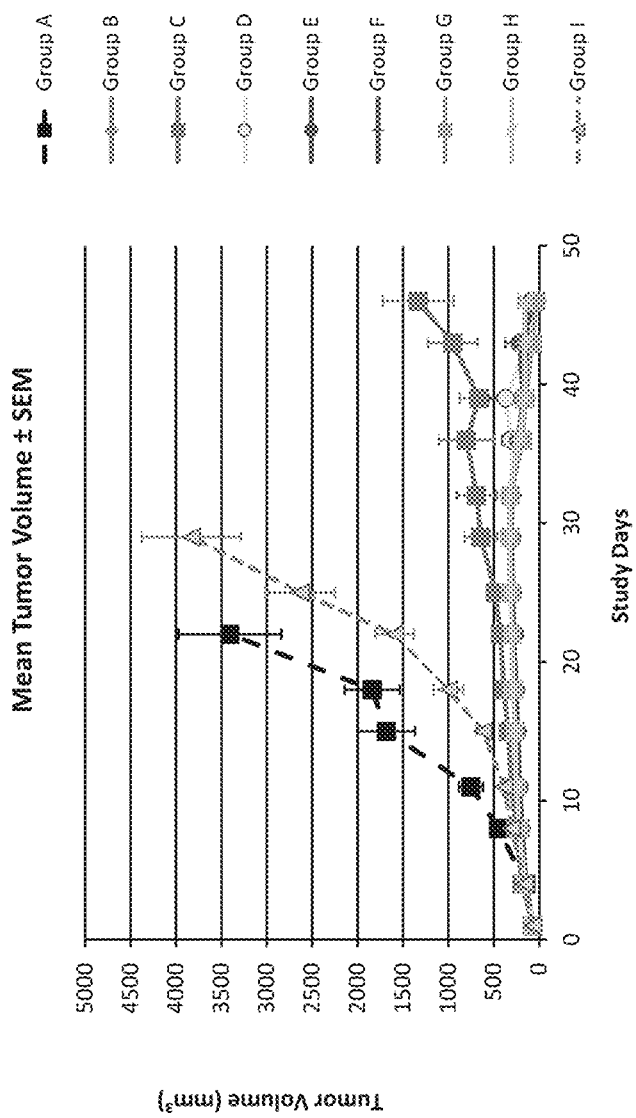
FIG. 1 is a graph depicting comparison data on efficacy of different mRNA-LNPs in in vivo anti-tumor activity. Mean tumor volume of each group was measured throughout the study after intratumoral administration of mRNA-LNPs to MC38 mice according to dose and frequency as shown in Table 2.

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Encapsulation: As used herein, the term "encapsulation," or grammatical equivalent, refers to the process of confining an individual mRNA molecule within a nanoparticle.

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

Messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides an improved mRNA therapeutics for the treatment for cancer. In particular, methods disclosed herein are effective in reducing or decreasing size, mass, and/or volume of a tumor or inhibiting or delaying the tumor growth in a subject in need thereof by administering, at an effective dose and an administration interval, a composition comprising one or more mRNAs encoding a protein or a peptide that directly or indirectly modulates immune response. In some embodiments, the methods disclosed herein increases survival.

Various aspects of the invention are described in detail in the following sections. The use of sections is not meant to limit the invention. Each section can apply to any aspect of the invention. In this application, the use of "or" means "and/or" unless stated otherwise.

Cancer

Cancerous cells express antigens that are not commonly expressed by non-cancerous cells or tissues. These cancer antigens are not presented by antigen presenting cells (APCs) in a manner similar to viral antigens, i.e. in association with the MHC-1 molecule categorizing the antigen as foreign, but cytotoxic T cells are able to differentiate and identify mutated self-antigens and possess an inherent property to seek and destroy cells that bear the mutated antigens. Therefore, one objective of cancer immunotherapy is to achieve optimum activation of cytotoxic T cells directed against the mutated antigens. Methods and compositions according to the present invention are effective in inducing a subject's own cytotoxic T cells to generate the necessary immune response to destroy tumor cells.

The normal tissue homeostasis is a highly regulated cell proliferation and cell death process. An imbalance of either cell or cell death proliferation can become a cancerous state (Solyanik et al., 1995; Stokke et al., 1997; Mumbyand Walter, 1991; Natoli et al., 1998; Magi-Galluzzi et al., 1998). For example, cervical cancer, kidney, lung, pancreatic, colorectal and brain are just a few examples of the many cancers that can result (Erlandsson, 1998; Kolmel, 1998; Mangrayand King, 1998; Gertig and Hunter, 1997; Mougin et al., 1998). In fact, the occurrence of cancer is so high that over 500,000 deaths per year are attributed to cancer in the United States.

The maintenance of cell proliferation and cell death is at least partially regulated by proto-oncogenes. Protooncogén can encode proteins that induce cellular proliferation (e.g., sis, erbB, src, ras and myc), proteins that inhibit cellular proliferation (e.g., Rb, p. 53, NF1 and WT1) or proteins that regulate death programmed cell (e.g., bcl-2) (Ochi et al., 1998; Johnson and Hamdy, 1998; Liebermann et al., 1998). However, genetic rearrangements or mutations to these proto-oncogenes, results in the conversion of a proto-onco-gene into a potent cancer causing oncogene. Often, a single point mutation is enough to transform a proto-oncogene into an oncogene. For example, a mutation in codon 12 or 13 in the K-ras gene can convert the proto-oncogene into an oncogene.

Currently, there are few effective for treating many common cancers options. The course of treatment for a given individual depends on the diagnosis, the stage to which the disease has developed and factors such as age, sex and general health of the patient. The most conventional options of cancer treatment are surgery, radiotherapy and chemotherapy. Surgery plays a key role in the diagnosis and treatment of cancer. Typically, a surgical approach is required for biopsy and to remove cancerous growth. However, if the cancer has metastasized and is widespread, surgery is unlikely to result in a cure and an alternate approach must be taken. Radiotherapy, chemotherapy and immunotherapy are alternatives to surgical treatment of cancer (Mayer, 1998; Ohara, 1998; Ho et al., 1998). Radiation therapy involves a precise targeting of high-energy radiation to destroy cancer and much like surgery way cells, it is effective primarily in the treatment of localized cancer cells, not metastasized. Side effects of radiation therapy include skin irritation, difficulty swallowing, dry mouth, nausea, diarrhea, hair loss and loss of energy (Curran, 1998; Brizel, 1998).

Chemotherapy, cancer treatment with anti-cancer drugs, is another mode of cancer therapy. The effectiveness of anticancer drug therapy is often limited because of the difficulty of achieving drug administration in all the (el-Kareh and Secomb, 1997) solid tumors. The Chemotherapeutic strategies are based on the growth of a solid tumor, wherein the anticancer drug selected as target cancer cells are rapidly dividing. Most chemotherapy approaches include the combination of more than one anti-cancer drug, which has been shown to increase the response rate of a wide variety of cancers. A major side effect of chemotherapy drugs is that they also affect normal tissue cells, with the cells is more likely to be affected rapidly dividing (eg, bone marrow, gastrointestinal tract, reproductive system and hair follicles). Other side effects of chemotherapy drugs are sores in the mouth, difficulty swallowing, dry mouth, nausea, diarrhea, vomiting, fatigue, bleeding, hair loss and infection. Other forms of chemotherapy can be used to treat non-cancerous hyperproliferative disorders. These include the use of conventional chemotherapeutics such as methotrexate and cyclophosphamide for hyperproliferative diseases such as rheumatoid arthritis and psoriasis. Paw chemotherapy hyperproliferative diseases can also include immunosuppressive agents such as steroids, azathioprine, cyclosporine and immunomodulatory agents such as fumaric acid derivatives.

Immunotherapy, rapidly evolving area in cancer research, is yet another option for treating certain types of cancers. For example, the immune system identifies tumor cells as foreign and therefore, are selected as target for destruction by the immune system. Unfortunately, the answer is usually not enough to prevent most tumor growths. However, recently there has been a focus in the area of immunotherapy to develop methods that augment or supplement the natural defense mechanisms of the immune system.

As mentioned earlier, proto-oncogenes play an important role in cancer biology. For example, Rb tumor suppressors, p53, NF1 and WT1 are essential for the maintenance of non-tumorigenic phenotype of cells (reviewed by Soddu and Sacchi, 1998). It has been found that approximately 50% of all cancers are associated with mutations of the p53 gene, resulting in the loss of the properties as tumor suppressor p53 (Levine et al., 1991; Vogelstein and Kinzler, 1992; Hartmann et al, 1996a; Hartmann et al, 1996b). The high incidence of mutations of the p53 gene in cancer has prompted many research groups to investigate p53 as a route of cancer treatment via gene transfer or replacement. Sis protooncogene, erbB, src, ras and myc, encoding proteins that induce cellular proliferation, and the proto-oncogenes of the Bcl-2 family that regulate programmed cell death also play important roles in the non-tumorigenic phenotype of cells.

In some embodiments, the cancer is head cancer, neck cancer, ovarian cancer, breast cancer, colon cancer, prostate cancer, liver cancer, leukemia, glioma, melanoma, pancreatic cancer, testicular cancer, melanoma, bladder cancer, lung cancer, sarcoma, squamous cell carcinoma, small cell lung cancer, a mammary gland ductal carcinoma, breast infiltrating carcinoma of lobular type, breast intraductal carcinoma, breast mucinous carcinoma, promyeocytic leukemia in the peripheral blood, an ovarian adenocarcinoma, an ovarian adenocarcinoma that has migrated into the abdominal cavity, a prostate adenocarinoma, a transitional cell carcinoma of the bladder, an epitheliod carcinoma in a pancreatic duct, an adenocarcinoma in a pancreatic duct, an adenocarcinoma in the cervical epithelium, cervical cancer, gastrointestinal cancer, urogenital cancer, brain cancer, mesothelioma, renal cell cancer, gynecological cancer, or endometrial cancer.

Cancer Treatment

In one aspect, the present invention provides methods for treating cancer. The methods disclosed herein are effective in reducing or decreasing size, mass, and/or volume of a tumor or inhibiting or delaying the tumor growth in a subject in need thereof by administering, at an effective dose and an administration interval, a composition comprising one or more mRNAs encoding a protein or a peptide that directly or indirectly modulates immune response. The methods disclosed herein are also effective in increasing survival of a subject. For example, in some embodiments, the methods and compositions described herein can increase the survival of a subject suffering from a cancer by between about 1 month and 12 months; 1 year and 5 years; 5 years and 10 years; 10 years and 15 years.

In one aspect, the present invention relates to methods of treating cancer via administration of mRNA encoding immune modulating proteins or peptides that are useful in immune-oncology (IO) Immune modulating proteins or peptides include Interleukin 1 (IL-1), IL-2, IL-3, IL-4, IL-5, IL-6, IL-7, IL-8, IL-10, IL-11, IL-12, IL-13, IL-15/15R, IL-18, IL-21, IL-27, macrophage inflammatory protein (MIP)-Iβ, MIP-1a, monocyte chemoattractant protein (MCP)-1, MCP-3, macrophage colony-stimulating factor (M-CSF), granulocyte-macrophage colony-stimulating factor (GM-CSF), RANTES (CCL5), Interferon (IFN)-γ, tumor necrosis factor (TNF)-α, granulocyte colony-stimulating factor (G-CSF), cluster of differentiation (CD) 80, CD86, EFNα, IFNp, IFN, FMS-like tyrosine kinase 3 ligand (FLT3L), NLR family pyrin domain containing 1 (NLRP1), NLRP3, stimulator of interferon genes (STING), absent in melanoma 2 (AIM2), Pyrin, IFN-inducible protein 16 (IFI16), and OX40L.

Tumor Size

Methods for treating cancer disclosed herein are effective in reducing the size of a tumor in a subject in need thereof as compared to a control. In some embodiments, the control is an untreated subject with same disease status. In some embodiments, the control is the subject prior to the administration. In some embodiments, the administration of the composition reduces the size of a tumor by at least 5% to 99% as compared to a control. In some embodiments, the administration of the composition reduces the size of a tumor by at least 5% as compared to a control. In some embodiments, the administration of the composition reduces the size of a tumor by at least 10% as compared to a control. In some embodiments, the administration of the composition reduces the size of a tumor by at least 15% as compared to a control. In some embodiments, the administration of the composition reduces the size of a tumor by at least 20% as compared to a control. In some embodiments, the administration of the composition reduces the size of a tumor by at least 25% as compared to a control. In some embodiments, the administration of the composition reduces the size of a tumor by at least 30% as compared to a control. In some embodiments, the administration of the composition reduces the size of a tumor by at least 35% as compared to a control. In some embodiments, the administration of the composition reduces the size of a tumor by at least 40% as compared to a control. In some embodiments, the administration of the composition reduces the size of a tumor by at least 45% as compared to a control. In some embodiments, the administration of the composition reduces the size of a tumor by at least 50% as compared to a control. In some embodiments, the administration of the composition reduces the size of a tumor by at least 60% as compared to a control. In some embodiments, the administration of the composition reduces the size of a tumor by at least 70% as compared to a control. In some embodiments, the administration of the composition reduces the size of a tumor by at least 80% as compared to a control. In some embodiments, the administration of the composition reduces the size of a tumor by at least 85% as compared to a control. In some embodiments, the administration of the composition reduces the size of a tumor by at least 90% as compared to a control. In some embodiments, the administration of the composition reduces the size of a tumor by at least 95% as compared to a control. In some embodiments, the administration of the composition reduces the size of a tumor by at least 99% as compared to a control. In some embodiments, the administration of the composition results in disappearance of a tumor.

In some embodiments, the administration of the composition reduces the size of a tumor 1 day post administration. In some embodiments, the administration of the composition reduces the size of a tumor 2 days post administration. In some embodiments, the administration of the composition reduces the size of a tumor 4 days post administration. In some embodiments, the administration of the composition reduces the size of a tumor 5 days post administration. In some embodiments, the administration of the composition reduces the size of a tumor 7 days post administration. In some embodiments, the administration of the composition reduces the size of a tumor 10 days post administration. In some embodiments, the administration of the composition reduces the size of a tumor 12 days post administration. In some embodiments, the administration of the composition reduces the size of a tumor 15 days post administration. In some embodiments, the administration of the composition reduces the size of a tumor 18 days post administration. In some embodiments, the administration of the composition reduces the size of a tumor 20 days post administration. In some embodiments, the administration of the composition reduces the size of a tumor 25 days post administration. In some embodiments, the administration of the composition reduces the size of a tumor 30 days post administration.

In some embodiments, the administration of the composition results in a reduced tumor size as compared to the control throughout the treatment period. In some embodiments, the administration of the composition results in a reduced tumor size as compared to the control for 5 days. In some embodiments, the administration of the composition results in a reduced tumor size as compared to the control for 7 days. In some embodiments, the administration of the composition results in a reduced tumor size as compared to the control for 10 days. In some embodiments, the administration of the composition results in a reduced tumor size as compared to the control for 15 days. In some embodiments, the administration of the composition results in a reduced tumor size as compared to the control for 20 days. In some embodiments, the administration of the composition results in a reduced tumor size as compared to the control for 25 days. In some embodiments, the administration of the composition results in a reduced tumor size as compared to the control for 30 days. In some embodiments, the administration of the composition results in a reduced tumor size as compared to the control for 35 days. In some embodiments, the administration of the composition results in a reduced tumor size as compared to the control for 40 days. In some embodiments, the administration of the composition results in a reduced tumor size as compared to the control for 45 days.

Tumor Growth Inhibition

Methods for treating cancer disclosed herein are effective in inhibiting or delaying the growth of tumor. Percent tumor growth inhibition is calculated by as follows: (mean(C)−mean(T))/mean(C)*100%, wherein T is the test group tumor volume and C is the control group tumor volume, wherein the control is the subject without treatment. In some embodiments, the method results in a percent tumor growth inhibition of greater than 5% to 99% relative to a control. In some embodiments, the method results in a percent tumor growth inhibition of greater than 5% relative to a control. In some embodiments, the method results in a percent tumor growth inhibition of greater than 10% relative to a control. In some embodiments, the method results in a percent tumor growth inhibition of greater than 15% relative to a control. In some embodiments, the method results in a percent tumor growth inhibition of greater than 20% relative to a control. In some embodiments, the method results in a percent tumor growth inhibition of greater than 25% relative to a control. In some embodiments, the method results in a percent tumor growth inhibition of greater than 30% relative to a control. In some embodiments, the method results in a percent tumor growth inhibition of greater than 35% relative to a control. In some embodiments, the method results in a percent tumor growth inhibition of greater than 40% relative to a control. In some embodiments, the method results in a percent tumor growth inhibition of greater than 45% relative to a control. In some embodiments, the method results in a percent tumor growth inhibition of greater than 50% relative to a control. In some embodiments, the method results in a percent tumor growth inhibition of greater than 60% relative to a control. In some embodiments, the method results in a percent tumor growth inhibition of greater than 70% relative to a control. In some embodiments, the method results in a percent tumor growth inhibition of greater than 75% relative to a control. In some embodiments, the method results in a percent tumor growth inhibition of greater than 80% relative to a control. In some embodiments, the method results in a percent tumor growth inhibition of greater than 85% relative to a control. In some embodiments, the method results in a percent tumor growth inhibition of greater than 90% relative to a control. In some embodiments, the method results in a percent tumor growth inhibition of greater than 95% relative to a control. In some embodiments, the method results in a percent tumor growth inhibition of greater than 99% relative to a control.

In some embodiments, the method results in inhibition of tumor growth 1 day after administration of an initial dose. In some embodiments, the method results in inhibition of tumor growth 3 days after administration of an initial dose. In some embodiments, the method results in inhibition of tumor growth 5 days after administration of an initial dose. In some embodiments, the method results in inhibition of tumor growth 7 days after administration of an initial dose. In some embodiments, the method results in inhibition of tumor growth 10 days after administration of an initial dose. In some embodiments, the method results in inhibition of tumor growth 15 days after administration of an initial dose. In some embodiments, the method results in inhibition of tumor growth 20 days after administration of an initial dose. In some embodiments, the method results in inhibition of tumor growth 25 days after administration of an initial dose. In some embodiments, the method results in inhibition of tumor growth 30 days after administration of an initial dose.

In some embodiments, the administration of the composition results in inhibition of tumor growth as compared to a control throughout the treatment period. In some embodiments, the administration of the composition results in inhibition of tumor growth as compared to a control 1 days. In some embodiments, the administration of the composition results in inhibition of tumor growth as compared to a control 5 days. In some embodiments, the administration of the composition results in inhibition of tumor growth as compared to a control 7 days. In some embodiments, the administration of the composition results in inhibition of tumor growth as compared to a control 10 days. In some embodiments, the administration of the composition results in inhibition of tumor growth as compared to a control 15 days. In some embodiments, the administration of the composition results in inhibition of tumor growth as compared to a control 20 days. In some embodiments, the administration of the composition results in inhibition of tumor growth as compared to a control 25 days. In some embodiments, the administration of the composition results in inhibition of tumor growth as compared to a control 30 days. In some embodiments, the administration of the composition results in inhibition of tumor growth as compared to a control 35 days. In some embodiments, the administration of the composition results in inhibition of tumor growth as compared to a control 40 days. In some embodiments, the administration of the composition results in inhibition of tumor growth as compared to a control 45 days.

In some embodiments, the method results in a percent tumor growth inhibition of greater than 50% relative to a control 5 days after administration of an initial dose. In some embodiments, the method results in a percent tumor growth inhibition of greater than 50% relative to a control 7 days after administration of an initial dose. In some embodiments, the method results in a percent tumor growth inhibition of greater than 60% relative to a control 5 days after administration of an initial dose. In some embodiments, the method results in a percent tumor growth inhibition of greater than 60% relative to a control 7 days after administration of an initial dose. In some embodiments, the method results in a percent tumor growth inhibition of greater than 50% relative to a control 10 days after administration of an initial dose. In some embodiments, the method results in a percent tumor growth inhibition of greater than 70% relative to a control 5 days after administration of an initial dose. In some embodiments, the method results in a percent tumor growth inhibition of greater than 70% relative to a control 7 days after administration of an initial dose. In some embodiments, the method results in a percent tumor growth inhibition of greater than 70% relative to a control 10 days after administration of an initial dose. In some embodiments, the method results in a percent tumor growth inhibition of greater than 80% relative to a control 5 days after administration of an initial dose. In some embodiments, the method results in a percent tumor growth inhibition of greater than 80% relative to a control 7 days after administration of an initial dose. In some embodiments, the method results in a percent tumor growth inhibition of greater than 80% relative to a control 10 days after administration of an initial dose. In some embodiments, the method results in a percent tumor growth inhibition of greater than 80% relative to a control 15 days after administration of an initial dose. In some embodiments, the method results in a percent tumor growth inhibition of greater than 80% relative to a control 20 days after administration of an initial dose. In some embodiments, the method results in a percent tumor growth inhibition of greater than 80% relative to a control 25 days after administration of an initial dose. In some embodiments, the method results in a percent tumor growth inhibition of greater than 85% relative to a control 7 days after administration of an initial dose. In some embodiments, the method results in a percent tumor growth inhibition of greater than 85% relative to a control 15 days after administration of an initial dose. In some embodiments, the method results in a percent tumor growth inhibition of greater than 85% relative to a control 20 days after administration of an initial dose. In some embodiments, the method results in a percent tumor growth inhibition of greater than 85% relative to a control 25 days after administration of an initial dose. In some embodiments, the method results in a percent tumor growth inhibition of greater than 90% relative to a control 7 days after administration of an initial dose. In some embodiments, the method results in a percent tumor growth inhibition of greater than 90% relative to a control 15 days after administration of an initial dose. In some embodiments, the method results in a percent tumor growth inhibition of greater than 90% relative to a control 20 days after administration of an initial dose. In some embodiments, the method results in a percent tumor growth inhibition of greater than 90% relative to a control 25 days after administration of an initial dose. In some embodiments, the method results in a percent tumor growth inhibition of greater than 95% relative to a control 7 days after administration of an initial dose. In some embodiments, the method results in a percent tumor growth inhibition of greater than 95% relative to a control 15 days after administration of an initial dose. In some embodiments, the method results in a percent tumor growth inhibition of greater than 95% relative to a control 20 days after administration of an initial dose. In some embodiments, the method results in a percent tumor growth inhibition of greater than 95% relative to a control 25 days after administration of an initial dose.

In some embodiments, the methods are effective in promoting an anti-tumor effect (e.g., induce T cell proliferation, induce T cell infiltration in a tumor, induce a memory T cell response, increasing the number of K cells, etc.) by administering the composition as described herein. In one embodiment, the present invention provides a method of activating T cells in a subject in need thereof, inducing T cell proliferation in a subject in need thereof, inducing T cell infiltration in a tumor of a subject in need thereof, and/or inducing a memory T cell response in a subject in need thereof, comprising administering to the subject a composition disclosed herein. In some embodiments, the administering of the compositions described herein, activates T cells in the subject. T cell activation can be characterized in any way known in the art. In some embodiments, the activated T cells express CD4. In some embodiments, the activated T cells express CD8. In certain embodiments the activated T cells express CD4 and CD8. In certain embodiments, the activated T cells comprise $CD4^+$ T cells, $CD8^+$ T cells, or both $CD4^+$ T cells and $CD8^+$ T cells. In some embodiments, T cell activation comprises increasing the number of tumor-infiltrating T cells. In certain embodiments, the number of tumor-infiltrating T cells in the tumor is increased by at least about 2 fold, at least about 3 fold, at least about 4 fold, at least about 5 fold, at least about 6 fold, at least about 7 fold, at least about 8 fold, at least about 9 fold, at least about 10 fold, at least about 20 fold, at least about 30 fold, at least about 50 fold, or at least about 100 fold, as compared to the number of tumor infiltrating T cells in the tumor prior to the administration of the composition.

Body Weight Change

Weight loss is common among subjects with cancer. Relieving side effects including weight loss is an important part of cancer care and treatment. In some embodiments, the administration of the composition results in a percent change of body weight in the subject of less than 60% to 1% relative to a control. In some embodiments the control is a body weight of the subject prior to the administration of the composition. In some embodiments, the administration of the composition results in a percent change of body weight in the subject of less than 60% relative to a control. In some embodiments, the administration of the composition results in a percent change of body weight in the subject of less than 50% relative to a control. In some embodiments, the administration of the composition results in a percent change of body weight in the subject of less than 40% relative to a control. In some embodiments, the administration of the composition results in a percent change of body weight in the subject of less than 30% relative to a control. In some embodiments, the administration of the composition results in a percent change of body weight in the subject of less than 25% relative to a control. In some embodiments, the administration of the composition results in a percent change of body weight in the subject of less than 20% relative to a control. In some embodiments, the administration of the composition results in a percent change of body weight in the subject of less than 15% relative to a control. In some embodiments, the administration of the composition results in a percent change of body weight in the subject of less than 10% relative to a control. In some embodiments, the administration of the composition results in a percent change of body weight in the subject of less than 5% relative to a control. In some embodiments, the administration of the composition results in a percent change of body weight in the subject of less than 1% relative to a control. In some embodiments, the administration of the composition results in substantially no change of body weight in the subject relative to a control.

Complete Response

In cancer treatment, long-term efficacy is another important factor. In some embodiment, the method results in complete remission, partial remission, stable disease, partial response, or complete response. In some embodiments, the complete response means that signs of cancer has disappeared or the inhibition of tumor growth has been maintained. In some embodiments, partial response refers to a degree of damage of multiple tumors has reduced in response to the treatment. The complete response rate is the percentage of subjects who exhibit complete response after the administration of the composition. In some embodiments, the complete response rate is greater than 50%. In some embodiments, the complete response rate is greater than 60%. In some embodiments, the complete response rate is greater than 70%. In some embodiments, the complete response rate is greater than 80%. In some embodiments, the complete response rate is greater than 85%. In some embodiments, the complete response rate is greater than 90%. In some embodiments, the complete response rate is greater than 95%. In some embodiments, the complete response rate is greater than 99%.

Dose and Administration Interval

As used herein, the term "therapeutically effective amount" is largely based on the total amount of the mRNA contained in the vaccine compositions of the present invention. Generally, a therapeutically effective amount is sufficient to achieve a meaningful benefit to the subject (e.g., treating, modulating, curing, inhibiting preventing and/or delaying cancer or its symptoms). For example, a therapeutically effective amount may be an amount sufficient to achieve a desired therapeutic and/or prophylactic effect. Generally, the amount of a therapeutic agent (e.g., mRNA encoding a protein or a peptide) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A delivery vehicle comprising mRNA may be administered and dosed in accordance with current medical practice, taking into account the clinical condition of the subject, the site and method of administration (e.g., local and systemic, including intratumoral, intravenous, and via injection), the scheduling of administration, the subject's age, sex, body weight, and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms (e.g., reduction in tumor size and/or inhibition of tumor growth) and other indicators as are selected as appropriate measures of cancer progress, regression or improvement by those of skill in the art.

In some embodiments, the method comprises injecting a single dose. In some embodiments, the method comprises injecting multiple doses periodically.

In some embodiments, a suitable dose ranges from 0.1 μg-100 mg mRNA. In some embodiments, the single dose or the multiple doses range from 0.1 μg-50 mg. In some embodiments, the single dose or the multiple doses range from 0.1 μg-25 mg. In some embodiments, the single dose or the multiple doses range from 0.1 μg-10 mg. In some embodiments, the single dose or the multiple doses range from 1-1 mg. In some embodiments, the single dose or the multiple doses range from 1-100 μg mRNA. In some embodiments, the single dose or the multiple dose is 0.1 μg. In some embodiments, the single dose or the multiple dose is 0.3 μg. In some embodiments, the single dose or the multiple dose is 0.5 μg. In some embodiments, the single dose or the multiple dose is 1 μg. In some embodiments, the single dose or the multiple dose is 5 μg. In some embodiments, the single dose or the multiple dose is 7.5 μg. In some embodiments, the single dose or the multiple dose is 10 μg. In some embodiments, the single dose or the multiple dose is 15 μg. In some embodiments, the single dose or the multiple dose is 20 μg. In some embodiments, the single dose or the multiple dose is 25 μg. In some embodiments, the single dose or the multiple dose is 30 μg. In some embodiments, the single dose or the multiple dose is 40 μg. In some embodiments, the single dose or the multiple dose is 50 μg. In some embodiments, the single dose or the multiple dose is 100 μg. In some embodiments, the single dose or the multiple dose is 1 mg. In some embodiments, the single dose or the multiple dose is 5 mg. In some embodiments, the single dose or the multiple dose is 7.5 mg. In some embodiments, the single dose or the multiple dose is 10 mg. In some embodiments, the single dose or the multiple dose is 20 mg. In some embodiments, the single dose or the multiple dose is 30 mg. In some embodiments, the single dose or the multiple dose is 50 mg. In some embodiments, the single dose or the multiple dose is 100 mg.

In some embodiments, the therapeutically effective dose ranges from about 0.005 mg/kg to 500 mg/kg body weight. In some embodiments, the therapeutically effective dose ranges from about 0.005 mg/kg to 400 mg/kg body weight. In some embodiments, the therapeutically effective dose ranges from about 0.005 mg/kg to 300 mg/kg body weight. In some embodiments, the therapeutically effective dose ranges from about 0.005 mg/kg to 200 mg/kg body weight. In some embodiments, the therapeutically effective dose ranges from about 0.005 mg/kg to 100 mg/kg body weight. In some embodiments, the therapeutically effective dose ranges from about 0.005 mg/kg to 90 mg/kg body weight. In some embodiments, the therapeutically effective dose ranges from about 0.005 mg/kg to 80 mg/kg body weight. In some embodiments, the therapeutically effective dose ranges from about 0.005 mg/kg to 70 mg/kg body weight. In some embodiments, the therapeutically effective dose ranges from about 0.005 mg/kg to 60 mg/kg body weight. In some embodiments, the therapeutically effective dose ranges from about 0.005 mg/kg to 50 mg/kg body weight. In some embodiments, the therapeutically effective dose ranges from about 0.005 mg/kg to 40 mg/kg body weight. In some embodiments, the therapeutically effective dose ranges from about 0.005 mg/kg to 30 mg/kg body weight. In some embodiments, the therapeutically effective dose ranges from about 0.005 mg/kg to 25 mg/kg body weight. In some embodiments, the therapeutically effective dose ranges from about 0.005 mg/kg to 20 mg/kg body weight. In some embodiments, the therapeutically effective dose ranges from about 0.005 mg/kg to 15 mg/kg body weight. In some embodiments, the therapeutically effective dose ranges from about 0.005 mg/kg to 10 mg/kg body weight.

In some embodiments, the therapeutically effective dose of the composition is greater than about 0.1 mg/kg body weight. In some embodiments, the therapeutically effective dose of the composition is greater than about 0.5 mg/kg body weight. In some embodiments, the therapeutically effective dose of the composition is greater than about 1.0 mg/kg body weight. In some embodiments, the therapeutically effective dose of the composition is greater than about 3 mg/kg body weight. In some embodiments, the therapeutically effective dose of the composition is greater than about 5 mg/kg body weight. In some embodiments, the therapeutically effective dose of the composition is greater than about 10 mg/kg body weight. In some embodiments, the therapeutically effective dose of the composition is greater than about 15 mg/kg body weight. In some embodiments, the therapeutically effective dose of the composition is greater than about 20 mg/kg body weight. In some embodiments, the therapeutically effective dose of the composition is greater than about 30 mg/kg body weight. In some embodiments, the therapeutically effective dose of the composition is greater than about 40 mg/kg body weight. In some embodiments, the therapeutically effective dose of the composition is greater than about 50 mg/kg body weight. In some embodiments, the therapeutically effective dose of the composition is greater than about 60 mg/kg body weight. In some embodiments, the therapeutically effective dose of the composition is greater than about 70 mg/kg body weight. In some embodiments, the therapeutically effective dose of the composition is greater than about 80 mg/kg body weight. In some embodiments, the therapeutically effective dose of the composition is greater than about 90 mg/kg body weight. In some embodiments, the therapeutically effective dose of the composition is greater than about 100 mg/kg body weight. In some embodiments, the therapeutically effective dose of the composition is greater than about 150 mg/kg body weight. In some embodiments, the therapeutically effective dose of the composition is greater than about 200 mg/kg body weight. In some embodiments, the therapeutically effective dose of the composition is greater than about 250 mg/kg body weight. In some embodiments, the therapeutically effective dose of the composition is greater than about 300 mg/kg body weight. In some embodiments, the therapeutically effective dose of the composition is greater than about 350 mg/kg body weight. In some embodiments, the therapeutically effective dose of the composition is greater than about 400 mg/kg body weight. In some embodiments, the therapeutically effective dose of the composition is greater than about 450 mg/kg body weight. In some embodiments, the therapeutically effective dose of the composition is greater than about 500 mg/kg body weight. In some embodiments, the therapeutically effective dose is 1.0 mg/kg body weight. In some embodiments, the therapeutically effective dose of 1.0 mg/kg body weight is administered subcutaneously, intramuscularly or intravenously.

Provided methods of the present invention contemplate single as well as multiple administrations of a therapeutically effective amount of the composition described herein. The composition can be administered at regular intervals, depending on the nature, severity and extent of the subject's condition, such as size of tumor, metastasis progress, or stage of cancer. In some embodiments, a therapeutically effective amount of the composition of the present invention may be administered periodically at regular intervals (e.g., daily, twice a week, once every four days, weekly, once every 10 days, biweekly, monthly, bimonthly, twice a month, once every 30 days, once every 28 days or continuously.

In some embodiments, provided liposomes and/or compositions are formulated such that they are suitable for extended-release of the mRNA contained therein. Such extended-release compositions may be conveniently administered to a subject at extended dosing intervals. For example, in some embodiments, the compositions of the present invention are administered to a subject twice a day. In some embodiments, the composition is administered to a subject twice a day. In some embodiments, the composition is administered to a subject daily. In some embodiments, the composition is administered to a subject every other day. In some embodiments, the composition is administered to a subject twice a week. In some embodiments, the composition is administered to a subject once a week. In some embodiments, the composition is administered to a subject once every 7 days. In some embodiments, the composition is administered to a subject once every 10 days. In some embodiments, the composition is administered to a subject once every 14 days. In some embodiments, the composition is administered to a subject once every 28 days. In some embodiments, the composition is administered to a subject once every 30 days. In some embodiments, the composition is administered to a subject once every two weeks. In some embodiments, the composition is administered to a subject once every three weeks. In some embodiments, the composition is administered to a subject once every four weeks. In some embodiments, the composition is administered to a subject once a month. In some embodiments, the composition is administered to a subject twice a month. In some embodiments, the composition is administered to a subject once every six weeks. In some embodiments, the composition is administered to a subject once every eight weeks. In some embodiments, the composition is administered to a subject once every other month. In some embodiments, the composition is administered to a subject once every three months. In some embodiments, the composition is administered to a subject once every four months. In some embodiments, the composition is administered to a subject once every six months. In some embodiments, the composition is administered to a subject once every eight months. In some embodiments, the composition is administered to a subject once every nine months. In some embodiments, the composition is administered to a subject annually. Also contemplated are compositions and liposomes which are formulated for depot administration (e.g., intramuscularly, subcutaneously, intravitreally) to either deliver or release mRNA over extended periods of time. Preferably, the extended-release means employed are combined with modifications made to the mRNA to enhance stability.

A therapeutically effective amount is commonly administered in a dosing regimen that may comprise multiple unit doses. For any particular vaccine, a therapeutically effective amount and administration interval (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific vaccine agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

In some embodiments, an initial dose and the subsequent dose or doses are same in amount. In some embodiments, an initial dose and the subsequent dose or doses are different in amount. In some embodiments, an initial dose is greater than the subsequent dose or doses. In some embodiments, an initial dose is less than the subsequent dose or doses. In some embodiments each of the multiple doses comprise the same dosage amount of mRNA. In some embodiments, each of the multiple doses comprise a different dosage amount of mRNA.

Composition of Invention

In one aspect, the present invention relates to methods of treating cancer via administration of a composition comprising one or more mRNAs encoding a protein or a peptide encapsulated within lipid nanoparticles. In one aspect, the present invention provides a pharmaceutical composition for treating cancer, comprising one or more mRNAs each encoding an immune modulating protein or a peptide, wherein one or more mRNAs are encapsulated within lipid nanoparticles. In some embodiments, the pharmaceutical composition comprises two or more mRNAs encoding one or more check point inhibitors.

mRNA

In some embodiments, the one or more mRNAs encode immune modulating proteins or peptides that are useful in immune-oncology (IO) Immune modulating proteins or peptides include Interleukin 1 (IL-1), IL-2, IL-3, IL-4, IL-5, IL-6, IL-7, IL-8, IL-10, IL-11, IL-12, IL-13, IL-15/15R, IL-18, IL-21, IL-27, macrophage inflammatory protein (MIP)-Iβ, MIP-1a, monocyte chemoattractant protein (MCP)-1, MCP-3, macrophage colony-stimulating factor (M-CSF), granulocyte-macrophage colony-stimulating factor (GM-CSF), RANTES (CCL5), Interferon (IFN)-γ, tumor necrosis factor (TNF)-α, granulocyte colony-stimulating factor (G-CSF), cluster of differentiation (CD) 80, CD86, EFNα, IFNp, IFN, FMS-like tyrosine kinase 3 ligand (FLT3L), NLR family pyrin domain containing 1 (NLRP1), NLRP3, stimulator of interferon genes (STING), absent in melanoma 2 (AIM2), Pyrin, IFN-inducible protein 16 (IFI16), and OX40L.

In some embodiments, the one or more mRNAs are codon optimized. In some embodiments, the protein or the peptide encoded by the mRNAs are wild-type. In some embodiments, the protein or the peptide encoded by the mRNAs contain a mutation or modification. In some embodiments, STING contains a R293M mutation. In some embodiments, NLRP3 contains a D301N mutation.

In some embodiments, the protein or the peptide encoded by the mRNAs modulates immune response. In some embodiments, the protein or the peptide is a fragment or a full-length cytokines. In some embodiments, a suitable protein or peptide is IL-1. In some embodiments, a suitable protein or peptide is IL-2. In some embodiments, a suitable protein or peptide is IL-3. In some embodiments, a suitable protein or peptide is IL-4. In some embodiments, a suitable protein or peptide is IL-5. In some embodiments, a suitable protein or peptide is IL-6. In some embodiments, a suitable protein or peptide is IL-7. In some embodiments, a suitable protein or peptide is IL-8. In some embodiments, a suitable protein or peptide is IL-10. In some embodiments, a suitable protein or peptide is IL-11. In some embodiments, a suitable protein or peptide is IL-12. In some embodiments, a suitable protein or peptide is IL-13. In some embodiments, a suitable protein or peptide is IL-15/15R. In some embodiments, a suitable protein or peptide is IL-18. In some embodiments, a suitable protein or peptide is IL-21. In some embodiments, a suitable protein or peptide is IL-27. In some embodiments, a suitable protein or peptide is MIP-Iβ. In some embodiments, a suitable protein or peptide is, MIP-1a. In some embodiments, a suitable protein or peptide is monocyte chemoattractant protein (MCP)-1. In some embodiments, a suitable protein or peptide is MCP-3. In some embodiments, a suitable protein or peptide is M-CSF. In some embodiments, a suitable protein or peptide is GM-CSF. In some embodiments, a suitable protein or peptide is RANTES or CCL5. In some embodiments, a suitable protein or peptide is IFN-γ. In some embodiments, a suitable protein or peptide is TNF-α. In some embodiments, a suitable protein or peptide is G-CSF. In some embodiments, a suitable protein or peptide is CD80. In some embodiments, a suitable protein or peptide is CD86. In some embodiments, a suitable protein or peptide is EFNα. In some embodiments, a suitable protein or peptide is IFNp. In some embodiments, a suitable protein or peptide is IFN. In some embodiments, a suitable protein or peptide is FLT3L. In some embodiments, a suitable protein or peptide is NLRP1. In some embodiments, a suitable protein or peptide is NLRP3. In some embodiments, a suitable protein or peptide is STING. In some embodiments, a suitable protein or peptide is AIM2. In some embodiments, a suitable protein or peptide is pyrin. In some embodiments, a suitable protein or peptide is IF116. In some embodiments, a suitable protein or peptide is OX40L.

In some embodiments, the one or more mRNAs encode IL-12 and STING. In some embodiments, the one or more mRNAs encode STING, IL-12, and GM-CS. In some embodiments, the one or more mRNAs encode STING, IL-12, FLT-3L, and GM-CSF. In some embodiments, the one or more mRNAs encode STING, IL-12, NLRP3, and GM-CSF. In some embodiments, the one or more mRNAs encode STING, IL-12, IL-2, and GM-CSF.

In one aspect, the present invention provides a method of treating cancer, comprising administering to a subject in need thereof a composition comprising two or more mRNAs each encoding a protein or a peptide encapsulated within lipid nanoparticles at an effective dose and an administration interval such that the a size of tumor is reduced or the growth of a tumor is inhibited. In some embodiments, the two or more mRNAs each encoding an immune modulating enzyme and/or a check point inhibitor. In some embodiments, a check point inhibitor inhibits PD1, PD-L1, CTLA-4, B7, BTLA, HVEM, TIM-3, GAL-9, LAG3, VISTA, KIR, 2B4, CD160, CGEN-15049, CHK1, CHK2, A2aR, or a combination thereof. In some embodiments, the suitable check point inhibitor inhibits PD1. In some embodiments, the suitable check point inhibitor inhibits PD-L1. In some embodiments, the suitable check point inhibitor inhibits CTLA-4. In some embodiments, the suitable check point inhibitor inhibits B7. In some embodiments, the suitable check point inhibitor inhibits BTLA. In some embodiments, the suitable check point inhibitor inhibits HVEM. In some embodiments, the suitable check point inhibitor inhibits TIM-3. In some embodiments, the suitable check point inhibitor inhibits GAL-9. In some embodiments, the suitable check point inhibitor inhibits LAG3. In some embodiments, the suitable check point inhibitor inhibits VISTA. In some embodiments, the suitable check point inhibitor inhibits KIR. In some embodiments, the suitable check point inhibitor inhibits 2B4. In some embodiments, the suitable check point inhibitor inhibits CD160. In some embodiments, the suitable check point inhibitor inhibits CGEN-15049. In some embodiments, the suitable check point inhibitor inhibits its CHK1. In some embodiments, the suitable check point inhibitor inhibits CHK2. In some embodiments, the suitable check point inhibitor inhibits A2aR. In some embodiments, the check point inhibitor is an antagonist against PD1, PD-L1, CTLA-4, B7, BTLA, HVEM, TIM-3, GAL-9, LAG3, VISTA, KIR, 2B4, CD160, CGEN-15049, CHK1, CHK2, A2aR, or a combination thereof. In some embodiments, the check point inhibitor is an antibody or a fragment thereof. In some embodiments, the antibody or a fragment thereof is humanized. In some embodiments, the composition comprises a checkpoint inhibitor.

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNAse inhibitor. The exact conditions will vary according to the specific application.

Exemplary Construct Design for mRNAs
Construct Design:
   X-mRNA Coding Region-Y
   5' and 3' UTR Sequences:

```
X (5' UTR Sequence) =
                                       (SEQ ID NO: 1)
GGACAGAUCGCCUGGAGACGCCAUCCACGCUGUUUUGACCUCCAUAGAAG

ACACCGGGACCGAUCCAGCCUCCGCGGCCGGGAACGGUGCAUUGGAACGC

GGAUUCCCCGUGCCAAGAGUGACUCACCGUCCUUGACACG

Y (3' UTR Sequence) =
                                       (SEQ ID NO: 2)
CGGGUGGCAUCCCUGUGACCCCUCCCCAGUGCCUCUCCUGGCCCUGGAAG

UUGCCACUCCAGUGCCCACCAGCCUUGUCCUAAUAAAAUUAAGUUGCAUC

AAGCU

OR
                                       (SEQ ID NO: 3)
GGGUGGCAUCCCUGUGACCCCUCCCCAGUGCCUCUCCUGGCCCUGGAAGU

UGCCACUCCAGUGCCCACCAGCCUUGUCCUAAUAAAAUUAAGUUGCAUCA

AAGCU
```

The present invention may be used to deliver mRNAs of a variety of lengths. In some embodiments, the present invention may be used to deliver in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to deliver in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Synthesis of mRNA Using SP6 RNA Polymerase

In some embodiments, mRNA is produced using SP6 RNA Polymerase. SP6 RNA Polymerase is a DNA-dependent RNA polymerase with high sequence specificity for SP6 promoter sequences. The SP6 polymerase catalyzes the 5'→3' in vitro synthesis of RNA on either single-stranded DNA or double-stranded DNA downstream from its promoter; it incorporates native ribonucleotides and/or modified ribonucleotides and/or labeled ribonucleotides into the polymerized transcript. Examples of such labeled ribonucleotides include biotin-, fluorescein-, digoxigenin-, aminoallyl-, and isotope-labeled nucleotides.

The sequence for bacteriophage SP6 RNA polymerase was initially described (GenBank: Y00105.1) as having the following amino acid sequence:

```
                                              (SEQ ID NO: 4)
MQDLHAIQLQLEEEMFNGGIRRFEADQQRQIAAGSESDTAWNRRLLSELI

APMAEGIQAYKEEYEGKKGRAPRALAFLQCVENEVAAYITMKVVMDMLNT

DATLQAIAMSVAERIEDQVRFSKLEGHAAKYFEKVKKSLKASRTKSYRHA

HNVAVVAEKSVAEKDADFDRWEAWPKETQLQIGTTLLEILEGSVFYNGEP

VFMRAMRTYGGKTIYYLQTSESVGQWISAFKEHVAQLSPAYAPCVIPPRP

WRTPFNGGFHTEKVASRIRLVKGNREHVRKLTQKQMPKVYKAINALQNTQ

WQINKDVLAVIEEVIRLDLGYGVPSFKPLIDKENKPANPVPVEFQHLRGR

ELKEMLSPEQWQQFINWKGECARLYTAETKRGSKSAAVVRMVGQARKYSA

FESIYFVYAMDSRSRVYVQSSTLSPQSNDLGKALLRFTEGRPVNGVEALK

WFCINGANLWGWDKKTFDVRVSNVLDEEFQDMCRDIAADPLTFTQWAKAD

APYEFLAWCFEYAQYLDLVDEGRADEFRTHLPVHQDGSCSGIQHYSAMLR

DEVGAKAVNLKPSDAPQDIYGAVAQVVIKKNALYMDADDATTFTSGSVTL

SGTELRAMASAWDSIGITRSLTKKPVMTLPYGSTRLTCRESVIDYIVDLE

EKEAQKAVAEGRTANKVHPFEDDRQDYLTPGAAYNYMTALIWPSISEVVK

APIVAMKMIRQLARFAAKRNEGLMYTLPTGFILEQKIMATEMLRVRTCLM

GDIKMSLQVETDIVDEAAMMGAAAPNFVHGHDASHLILTVCELVDKGVTS

IAVIHDSFGTHADNTLTLRVALKGQMVAMYIDGNALQKLLEEHEVRWMVD

TGIEVPEQGEFDLNEIMDSEYVFA.
```

An SP6 RNA polymerase suitable for the present invention can be any enzyme having substantially the same polymerase activity as bacteriophage SP6 RNA polymerase. Thus, in some embodiments, an SP6 RNA polymerase suitable for the present invention may be modified from SEQ ID NO: 4. For example, a suitable SP6 RNA polymerase may contain one or more amino acid substitutions, deletions, or additions. In some embodiments, a suitable SP6 RNA polymerase has an amino acid sequence about 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, or 60% identical or homologous to SEQ ID NO: 4. In some embodiments, a suitable SP6 RNA polymerase may be a truncated protein (from N-terminus, C-terminus, or internally) but retain the polymerase activity. In some embodiments, a suitable SP6 RNA polymerase is a fusion protein.

An SP6 RNA polymerase suitable for the invention may be a commercially-available product, e.g., from Aldevron, Ambion, New England Biolabs (NEB), Promega, and Roche. The SP6 may be ordered and/or custom designed from a commercial source or a non-commercial source according to the amino acid sequence of SEQ ID NO: 4 or a variant of SEQ ID NO: 4 as described herein. The SP6 may be a standard-fidelity polymerase or may be a high-fidelity/high-efficiency/high-capacity which has been modified to promote RNA polymerase activities, e.g., mutations in the SP6 RNA polymerase gene or post-translational modifications of the SP6 RNA polymerase itself. Examples of such modified SP6 include SP6 RNA Polymerase-Plus™ from Ambion, HiScribe SP6 from NEB, and RiboMAX™ and Riboprobe® Systems from Promega.

In some embodiments, a suitable SP6 RNA polymerase is a fusion protein. For example, an SP6 RNA polymerase may include one or more tags to promote isolation, purification, or solubility of the enzyme. A suitable tag may be located at the N-terminus, C-terminus, and/or internally. Non-limiting examples of a suitable tag include Calmodulin-binding protein (CBP); *Fasciola hepatica* 8-kDa antigen (Fh8); FLAG tag peptide; glutathione-S-transferase (GST); Histidine tag (e.g., hexahistidine tag (His6)); maltose-binding protein (MBP); N-utilization substance (NusA); small ubiquitin related modifier (SUMO) fusion tag; Streptavidin binding peptide (STREP); Tandem affinity purification (TAP); and thioredoxin (TrxA). Other tags may be used in the present invention. These and other fusion tags have been described, e.g., Costa et al. Frontiers in Microbiology 5 (2014): 63 and in PCT/US16/57044, the contents of which are incorporated herein by reference in their entireties. In certain embodiments, a His tag is located at SP6's N-terminus.

SP6 Promoter

Any promoter that can be recognized by an SP6 RNA polymerase may be used in the present invention. Typically, an SP6 promoter comprises 5' ATTTAGGTGACACTATAG-3' (SEQ ID NO: 5). Variants of the SP6 promoter have been discovered and/or created to optimize recognition and/or binding of SP6 to its promoter. Non-limiting variants include but are not limited to:

```
                        (SEQ ID NO: 6 to SEQ ID NO: 15)
    5'-ATTTAGGGGACACTATAGAAGAG-3';

5'-ATTTAGGGGACACTATAGAAGG-3';

5'-ATTTAGGGGACACTATAGAAGGG-3';

5'-ATTTAGGTGACACTATAGAA-3';

5'-ATTTAGGTGACACTATAGAAGA-3';

5'-ATTTAGGTGACACTATAGAAGAG-3';

5'-ATTTAGGTGACACTATAGAAGG-3';

5'-ATTTAGGTGACACTATAGAAGGG-3';

5'-ATTTAGGTGACACTATAGAAGNG-3';
    and

5'-CATACGATTTAGGTGACACTATAG-3'.
```

In addition, a suitable SP6 promoter for the present invention may be about 95%, 90%, 85%, 80%, 75%, or 70% identical or homologous to any one of SEQ ID NO: 5 to SEQ ID NO: 15. Moreover, an SP6 promoter useful in the present invention may include one or more additional nucleotides 5' and/or 3' to any of the promoter sequences described herein.

DNA Template

Typically, a DNA template is either entirely double-stranded or mostly single-stranded with a double-stranded SP6 promoter sequence.

Linearized plasmid DNA (linearized via one or more restriction enzymes), linearized genomic DNA fragments (via restriction enzyme and/or physical means), PCR products, and/or synthetic DNA oligonucleotides can be used as templates for in vitro transcription with SP6, provided that they contain a double-stranded SP6 promoter upstream (and in the correct orientation) of the DNA sequence to be transcribed.

In some embodiments, the linearized DNA template has a blunt-end.

In some embodiments, the DNA sequence to be transcribed may be optimized to facilitate more efficient transcription and/or translation. For example, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, RNA instability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding. Optimization methods known in the art may be used in the present invention, e.g., GeneOptimizer by ThermoFisher and OptimumGene™, which are described in US 20110081708, the contents of which are incorporated herein by reference in its entirety.

In some embodiments, the DNA template includes a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Large-Scale mRNA Synthesis

The present invention relates to large-scale production of wild-type or codon optimized mRNAs. In some embodiments, a method according to the invention synthesizes mRNA at least 100 mg, 150 mg, 200 mg, 300 mg, 400 mg, 500 mg, 600 mg, 700 mg, 800 mg, 900 mg, 1 g, 5 g, 10 g, 25 g, 50 g, 75 g, 100 g, 250 g, 500 g, 750 g, 1 kg, 5 kg, 10 kg, 50 kg, 100 kg, 1000 kg, or more at a single batch. As used herein, the term "batch" refers to a quantity or amount of mRNA synthesized at one time, e.g., produced according to a single manufacturing setting. A batch may refer to an amount of mRNA synthesized in one reaction that occurs via a single aliquot of enzyme and/or a single aliquot of DNA template for continuous synthesis under one set of conditions. mRNA synthesized at a single batch would not include mRNA synthesized at different times that are combined to achieve the desired amount. Generally, a reaction mixture includes SP6 RNA polymerase, a linear DNA template, and an RNA polymerase reaction buffer (which may include ribonucleotides or may require addition of ribonucleotides).

According to the present invention, 1-100 mg of SP6 polymerase is typically used per gram (g) of mRNA produced. In some embodiments, about 1-90 mg, 1-80 mg, 1-60 mg, 1-50 mg, 1-40 mg, 10-100 mg, 10-80 mg, 10-60 mg, 10-50 mg of SP6 polymerase is used per gram of mRNA produced. In some embodiments, about 5-20 mg of SP6 polymerase is used to produce about 1 gram of mRNA. In some embodiments, about 0.5 to 2 grams of SP6 polymerase is used to produce about 100 grams of mRNA. In some embodiments, about 5 to 20 grams of SP6 polymerase is used to about 1 kilogram of mRNA. In some embodiments, at least 5 mg of SP6 polymerase is used to produce at least 1 gram of mRNA. In some embodiments, at least 500 mg of SP6 polymerase is used to produce at least 100 grams of mRNA. In some embodiments, at least 5 grams of SP6 polymerase is used to produce at least 1 kilogram of mRNA. In some embodiments, about 10 mg, 20 mg, 30 mg, 40 mg, 50 mg, 60 mg, 70 mg, 80 mg, 90 mg, or 100 mg of plasmid DNA is used per gram of mRNA produced. In some embodiments, about 10-30 mg of plasmid DNA is used to produce about 1 gram of mRNA. In some embodiments, about 1 to 3 grams of plasmid DNA is used to produce about 100 grams of mRNA. In some embodiments, about 10 to 30 grams of plasmid DNA is used to about 1 kilogram of mRNA. In some embodiments, at least 10 mg of plasmid DNA is used to produce at least 1 gram of mRNA. In some embodiments, at least 1 gram of plasmid DNA is used to produce at least 100 grams of mRNA. In some embodiments, at least 10 grams of plasmid DNA is used to produce at least 1 kilogram of mRNA.

In some embodiments, the concentration of the SP6 RNA polymerase in the reaction mixture may be from about 1 to 100 nM, 1 to 90 nM, 1 to 80 nM, 1 to 70 nM, 1 to 60 nM, 1 to 50 nM, 1 to 40 nM, 1 to 30 nM, 1 to 20 nM, or about 1 to 10 nM. In certain embodiments, the concentration of the SP6 RNA polymerase is from about 10 to 50 nM, 20 to 50 nM, or 30 to 50 nM. A concentration of 100 to 10000 Units/ml of the SP6 RNA polymerase may be used, as examples, concentrations of 100 to 9000 Units/ml, 100 to 8000 Units/ml, 100 to 7000 Units/ml, 100 to 6000 Units/ml, 100 to 5000 Units/ml, 100 to 1000 Units/ml, 200 to 2000 Units/ml, 500 to 1000 Units/ml, 500 to 2000 Units/ml, 500 to 3000 Units/ml, 500 to 4000 Units/ml, 500 to 5000

Units/ml, 500 to 6000 Units/ml, 1000 to 7500 Units/ml, and 2500 to 5000 Units/ml may be used.

The concentration of each ribonucleotide (e.g., ATP, UTP, GTP, and CTP) in a reaction mixture is between about 0.1 mM and about 10 mM, e.g., between about 1 mM and about 10 mM, between about 2 mM and about 10 mM, between about 3 mM and about 10 mM, between about 1 mM and about 8 mM, between about 1 mM and about 6 mM, between about 3 mM and about 10 mM, between about 3 mM and about 8 mM, between about 3 mM and about 6 mM, between about 4 mM and about 5 mM. In some embodiments, each ribonucleotide is at about 5 mM in a reaction mixture. In some embodiments, the total concentration of rNTPs (for example, ATP, GTP, CTP and UTPs combined) used in the reaction range between 1 mM and 40 mM. In some embodiments, the total concentration of rNTPs (for example, ATP, GTP, CTP and UTPs combined) used in the reaction range between 1 mM and 30 mM, or between 1 mM and 28 mM, or between 1 mM to 25 mM, or between 1 mM and 20 mM. In some embodiments, the total rNTPs concentration is less than 30 mM. In some embodiments, the total rNTPs concentration is less than 25 mM. In some embodiments, the total rNTPs concentration is less than 20 mM. In some embodiments, the total rNTPs concentration is less than 15 mM. In some embodiments, the total rNTPs concentration is less than 10 mM.

The RNA polymerase reaction buffer typically includes a salt/buffering agent, e.g., Tris, HEPES, ammonium sulfate, sodium bicarbonate, sodium citrate, sodium acetate, potassium phosphate sodium phosphate, sodium chloride, and magnesium chloride.

The pH of the reaction mixture may be between about 6 to 8.5, from 6.5 to 8.0, from 7.0 to 7.5, and in some embodiments, the pH is 7.5.

Linear or linearized DNA template (e.g., as described above and in an amount/concentration sufficient to provide a desired amount of RNA), the RNA polymerase reaction buffer, and SP6 RNA polymerase are combined to form the reaction mixture. The reaction mixture is incubated at between about 37° C. and about 42° C. for thirty minutes to six hours, e.g., about sixty to about ninety minutes.

In some embodiments, about 5 mM NTPs, about 0.05 mg/mL SP6 polymerase, and about 0.1 mg/ml DNA template in a suitable RNA polymerase reaction buffer (final reaction mixture pH of about 7.5) is incubated at about 37° C. to about 42° C. for sixty to ninety minutes.

In some embodiments, a reaction mixture contains linearized double stranded DNA template with an SP6 polymerase-specific promoter, SP6 RNA polymerase, RNase inhibitor, pyrophosphatase, 29 mM NTPs, 10 mM DTT and a reaction buffer (when at 10× is 800 mM HEPES, 20 mM spermidine, 250 mM $MgCl_2$, pH 7.7) and quantity sufficient (QS) to a desired reaction volume with RNase-free water; this reaction mixture is then incubated at 37° C. for 60 minutes. The polymerase reaction is then quenched by addition of DNase I and a DNase I buffer (when at 10× is 100 mM Tris-HCl, 5 mM $MgCl_2$ and 25 mM $CaCl_2$, pH 7.6) to facilitate digestion of the double-stranded DNA template in preparation for purification. This embodiment has been shown to be sufficient to produce 100 grams of mRNA.

In some embodiments, a reaction mixture includes NTPs at a concentration ranging from 1-10 mM, DNA template at a concentration ranging from 0.01-0.5 mg/ml, and SP6 RNA polymerase at a concentration ranging from 0.01-0.1 mg/ml, e.g., the reaction mixture comprises NTPs at a concentration of 5 mM, the DNA template at a concentration of 0.1 mg/ml, and the SP6 RNA polymerase at a concentration of 0.05 mg/ml.

Nucleotides

Various naturally-occurring or modified nucleosides may be used to product mRNA according to the present invention. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, pseudouridine, (e.g., N-1-methyl-pseudouridine), 2-thiouridine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, the mRNA comprises one or more nonstandard nucleotide residues. The nonstandard nucleotide residues may include, e.g., 5-methyl-cytidine ("5mC"), pseudouridine ("ψU"), and/or 2-thio-uridine ("2sU"). See, e.g., U.S. Pat. No. 8,278,036 or WO2011012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US20120195936 and international publication WO2011012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Some embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In some embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In some embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

Post-Synthesis Processing

Typically, a 5' cap and/or a 3' tail may be added after the synthesis. The presence of the cap is important in providing resistance to nucleases found in most eukaryotic cells. The presence of a "tail" serves to protect the mRNA from exonuclease degradation.

A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A, G(5')ppp(5')A and G(5')ppp(5')G. Additional cap structures are described in published US Application No. US 2016/0032356 and U.S. Provisional Application 62/464,327, filed Feb. 27, 2017, which are incorporated herein by reference.

Typically, a tail structure includes a poly(A) and/or poly (C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly A or poly C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly (A) and poly (C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

As described herein, the addition of the 5' cap and/or the 3' tail facilitates the detection of abortive transcripts generated during in vitro synthesis because without capping and/or tailing, the size of those prematurely aborted mRNA transcripts can be too small to be detected. Thus, in some embodiments, the 5' cap and/or the 3' tail are added to the synthesized mRNA before the mRNA is tested for purity (e.g., the level of abortive transcripts present in the mRNA). In some embodiments, the 5' cap and/or the 3' tail are added to the synthesized mRNA before the mRNA is purified as described herein. In other embodiments, the 5' cap and/or the 3' tail are added to the synthesized mRNA after the mRNA is purified as described herein.

mRNA synthesized according to the present invention may be used without further purification. In particular, mRNA synthesized according to the present invention may be used without a step of removing shortmers. In some embodiments, mRNA synthesized according to the present invention may be further purified. Various methods may be used to purify mRNA synthesized according to the present invention. For example, purification of mRNA can be performed using centrifugation, filtration and/or chromatographic methods. In some embodiments, the synthesized mRNA is purified by ethanol precipitation or filtration or chromatography, or gel purification or any other suitable means. In some embodiments, the mRNA is purified by HPLC. In some embodiments, the mRNA is extracted in a standard phenol:chloroform:isoamyl alcohol solution, well known to one of skill in the art. In some embodiments, the mRNA is purified using Tangential Flow Filtration. Suitable purification methods include those described in US 2016/0040154, US 2015/0376220, PCT application PCT/US18/19954 entitled "METHODS FOR PURIFICATION OF MESSENGER RNA" filed on Feb. 27, 2018, and PCT application PCT/US18/19978 entitled "METHODS FOR PURIFICATION OF MESSENGER RNA" filed on Feb. 27, 2018, all of which are incorporated by reference herein and may be used to practice the present invention.

In some embodiments, the mRNA is purified before capping and tailing. In some embodiments, the mRNA is purified after capping and tailing. In some embodiments, the mRNA is purified both before and after capping and tailing.

In some embodiments, the mRNA is purified either before or after or both before and after capping and tailing, by centrifugation.

In some embodiments, the mRNA is purified either before or after or both before and after capping and tailing, by filtration.

In some embodiments, the mRNA is purified either before or after or both before and after capping and tailing, by Tangential Flow Filtration (TFF).

In some embodiments, the mRNA is purified either before or after or both before and after capping and tailing by chromatography.

Characterization of mRNA

Full-length or abortive transcripts of mRNA may be detected and quantified using any methods available in the art. In some embodiments, the synthesized mRNA molecules are detected using blotting, capillary electrophoresis, chromatography, fluorescence, gel electrophoresis, HPLC, silver stain, spectroscopy, ultraviolet (UV), or UPLC, or a combination thereof. Other detection methods known in the art are included in the present invention. In some embodiments, the synthesized mRNA molecules are detected using UV absorption spectroscopy with separation by capillary electrophoresis. In some embodiments, mRNA is first denatured by a Glyoxal dye before gel electrophoresis ("Glyoxal gel electrophoresis"). In some embodiments, synthesized mRNA is characterized before capping or tailing. In some embodiments, synthesized mRNA is characterized after capping and tailing.

In some embodiments, mRNA generated by the method disclosed herein comprises less than 10%, less than 9%, less than 8%, less than 7%, less than 6%, less than 5%, less than 4%, less than 3%, less than 2%, less than 1%, less than 0.5%, less than 0.1% impurities other than full length mRNA. The impurities include IVT contaminants, e.g., proteins, enzymes, free nucleotides and/or shortmers.

In some embodiments, mRNA produced according to the invention is substantially free of shortmers or abortive transcripts. In particular, mRNA produced according to the invention contains undetectable level of shortmers or abortive transcripts by capillary electrophoresis or Glyoxal gel electrophoresis. As used herein, the term "shortmers" or "abortive transcripts" refers to any transcripts that are less than full-length. In some embodiments, "shortmers" or "abortive transcripts" are less than 100 nucleotides in length, less than 90, less than 80, less than 70, less than 60, less than 50, less than 40, less than 30, less than 20, or less than 10 nucleotides in length. In some embodiments, shortmers are detected or quantified after adding a 5'-cap, and/or a 3'-poly A tail.

Delivery Vehicles

According to the present invention, mRNA encoding a protein or a peptide (e.g., a full length, fragment, or portion of a protein or a peptide) as described herein may be delivered as naked RNA (unpackaged) or via delivery vehicles. As used herein, the terms "delivery vehicle," "transfer vehicle," "nanoparticle" or grammatical equivalent, are used interchangeably.

Delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. A particular delivery vehicle is selected based upon its ability to facilitate the transfection of a nucleic acid to a target cell.

In some embodiments, a delivery vehicle comprising one or more mRNAs is administered by intravenous, intratumoral, intradermal, subcutaneous, intramuscular, intraperitoneal, epideural, intrathecal, or pulmonary delivery, e.g., comprising nebulization.

In some embodiments, the mRNA is expressed in the tissue in which the delivery vehicle was administered. Additional teaching of pulmonary delivery and nebulization are described in the related international application PCT/US17/61100 filed Nov. 10, 2017 by Applicant entitled "NOVEL ICE-BASED LIPID NANOPARTICLE FORMULATION FOR DELIVERY OF MRNA", and the U. S. Provisional Application U.S. Ser. No. 62/507,061, each of which is incorporated by reference in its entirety.

In some embodiments, mRNAs encoding a protein or a peptide may be delivered via a single delivery vehicle. In some embodiments, mRNAs encoding a protein or a peptide may be delivered via one or more delivery vehicles each of a different composition. In some embodiments, the one or more mRNAs are encapsulated within the same lipid nanoparticles. In some embodiments, the one or more mRNAs are encapsulated within separate lipid nanoparticles.

According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphorsilicate nanoparticulates, calcium phosphate nanoparticulates, silicon dioxide nanoparticulates, nanocrystalline particulates, semiconductor nanoparticulates, poly (D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags. Also contemplated is the use of bionanocapsules and other viral capsid proteins assemblies as a suitable transfer vehicle. (Hum. Gene Ther. 2008 September; 19(9):887-95).

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). In the context of the present invention, a liposomal delivery vehicle typically serves to transport a desired mRNA to a target cell or tissue. In some embodiments, a nanoparticle delivery vehicle is a liposome. In some embodiments, a liposome comprises one or more cationic lipids, one or more non-cationic lipids, one or more cholesterol-based lipids and one or more PEG-modified lipids. In some embodiments, a liposome comprises no more than three distinct lipid components. In some embodiments, one distinct lipid component is a sterol-based cationic lipid.

Cationic Lipids

In some embodiments, liposomes may comprise one or more cationic lipids. As used herein, the phrase "cationic lipid" refers to any of a number of lipid species that have a net positive charge at a selected pH, such as physiological pH. Several cationic lipids have been described in the literature, many of which are commercially available. An example of suitable cationic lipids for use in the compositions and methods of the invention include those described in international patent publications WO 2010/053572 (for example, CI 2-200 described at paragraph [00225]) and WO 2012/170930, both of which are incorporated herein by reference. In certain embodiments, the compositions and methods of the invention employ a lipid nanoparticles comprising an ionizable cationic lipid described in U.S. provisional patent application 61/617,468, filed Mar. 29, 2012 (incorporated herein by reference), such as, e.g, (15Z, 18Z)—N,N-dimethyl-6-(9Z, 12Z)-octadeca-9, 12-dien-1-yl) tetracosa-15,18-dien-1-amine (HGT5000), (15Z, 18Z)—N, N-dimethyl-6-((9Z, 12Z)-octadeca-9, 12-dien-1-yl)tetracosa-4,15,18-trien-1-amine (HGT5001), and (15Z,18Z)—N,N-dimethyl-6-((9Z, 12Z)-octadeca-9, 12-dien-1-yl) tetracosa-5, 15, 18-trien-1-amine (HGT5002).

In some embodiments, provided liposomes include a cationic lipid described in WO 2013/063468 and in U.S. provisional application entitled "Lipid Formulations for Delivery of Messenger RNA" filed concurrently with the present application on even date, both of which are incorporated by reference herein.

In some embodiments, a cationic lipid comprises a compound of formula I-c1-a:

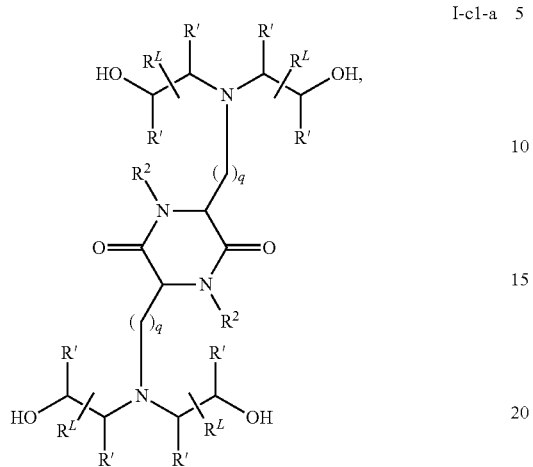

I-c1-a or a pharmaceutically acceptable salt thereof, wherein:

each $R^2$ independently is hydrogen or $C_{1-3}$ alkyl;

each q independently is 2 to 6;

each R' independently is hydrogen or $C_{1-3}$ alkyl;

and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R independently is hydrogen or methyl; and each $R^L$ independently is $C_{8-12}$ alkyl.

In some embodiments, each $R^2$ is hydrogen; each q independently is 3 to 5; each R is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

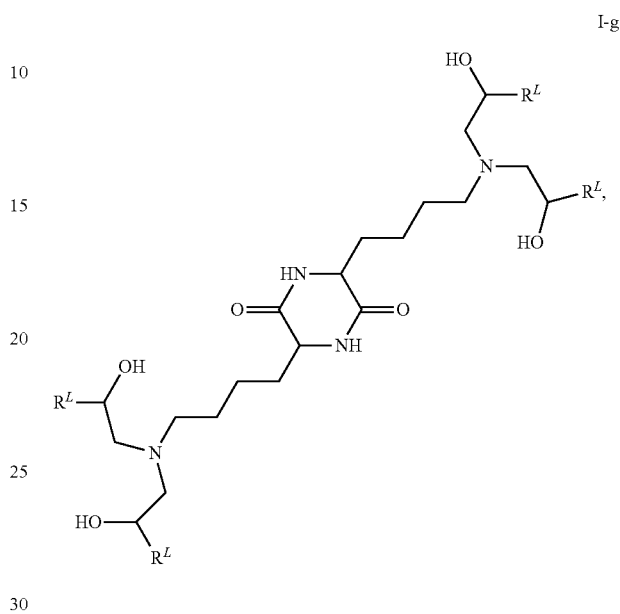

I-g or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, provided liposomes include a cationic lipid cKK-E12, or (3,6-bis(4-(bis(2-hydroxydodecyl)amino)butyl)piperazine-2,5-dione). The structure of cKK-E12 is shown below:

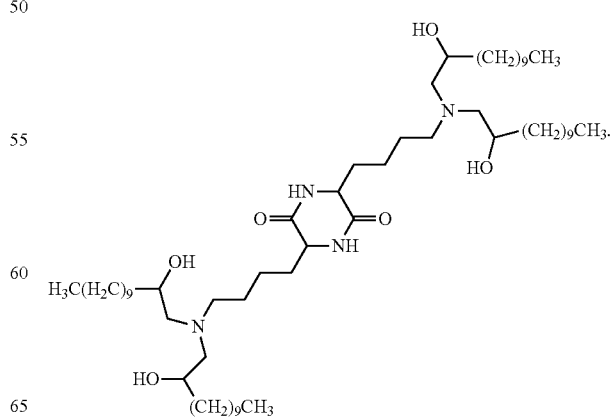

Additional exemplary cationic lipids include those of formula I:

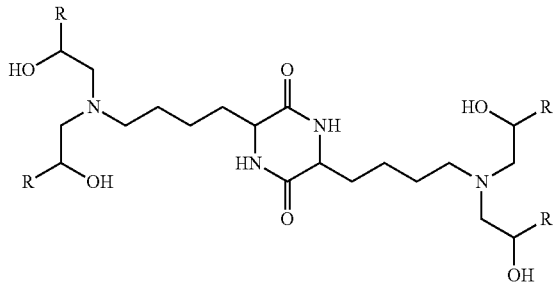

and pharmaceutically acceptable salts thereof, wherein,
R is

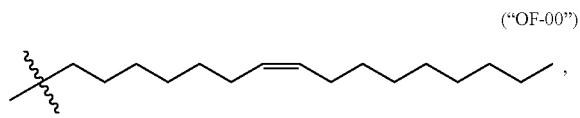 [SMILES: *CCCCCC/C=C\CCCCCCCC]

("OF-00")

R is

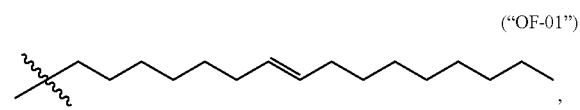 [SMILES: *CCCCCC/C=C/CCCCCCCC]

("OF-01")

R is

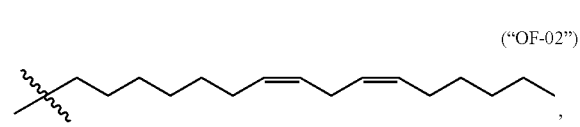 [SMILES: *CCCCCC/C=C\C/C=C\CCCCC]

("OF-02")

or
R is

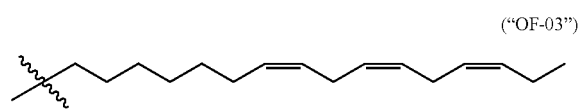 [SMILES: *CCCCCC/C=C\C/C=C\C/C=C\CC]

("OF-03")

(see, e.g., Fenton, Owen S., et al. "Bioinspired Alkenyl Amino Alcohol Ionizable Lipid Materials for Highly Potent In Vivo mRNA Delivery." *Advanced materials* (2016)).

In some embodiments, the one or more cationic lipids may be N-[1-(2,3-dioleyloxy)propyl]-N,N,N-trimethylammonium chloride or "DOTMA" (Feigner et al. (Proc. Nat'l Acad. Sci. 84, 7413 (1987); U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido) ethyl]-N,N-dimethyl-l-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethyl-arnrnonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethy 1-1-(cis,cis-9', 1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin--DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1). In some embodiments, one or more of the cationic lipids comprise at least one of an imidazole, dialkylamino, or guanidinium moiety.

In some embodiments, the one or more cationic lipids may be chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)-N,N-dimethyl-2,2-dn(9Z, 12Z)-octadeca-9,12-dienyl)tetrahydro-3aH-cyclopenta[d] [1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO 2012/170889, the teachings of which are incorporated herein by reference in their entirety), ICE (WO 2011/068810, the teachings of which are incorporated herein by reference in their entirety), HGT5000 (U.S. Provisional Patent Application No. 61/617, 468, the teachings of which are incorporated herein by reference in their entirety) or HGT5001 (cis or trans) (Provisional Patent Application No. 61/617,468), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Ra. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869).

Sterol Cationic Lipids

In some embodiments, sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by structure (II) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta[a]phenanthren-3-yl 3-(1H-imidazol-4-yl)propanoate, as represented by structure (II).

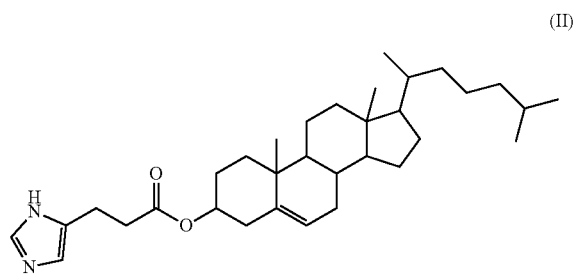 [SMILES: CC(C)CCCC(C)C1CCC2C3CC=C4CC(OC(=O)CCc5cnc[nH]5)CCC4(C)C3CCC12C]

(II)

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, or about 50% of the liposome by molar ratio.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other lipids, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the lipid nanoparticle may be greater than 5%, greater than 10%, greater than 20%, greater than 30%, or greater than 40%.

PEG-Modified Lipids

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle). Contemplated PEG-modified lipids include, but are not limited to, a polyethylene glycol chain of up to S kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the MCNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

A suitable liposome for the present invention may include one or more of any of the cationic lipids, non-cationic lipids, cholesterol lipids, PEG-modified lipids and/or polymers described herein at various ratios. As non-limiting examples, a suitable liposome formulation may include a combination selected from cKK-E12, DOPE, cholesterol and DMG-PEG2K; C12-200, DOPE, cholesterol and DMG-PEG2K; HGT4003, DOPE, cholesterol and DMG-PEG2K; ICE, DOPE, cholesterol and DMG-PEG2K; or ICE, DOPE, and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5.

Ratio of Distinct Lipid Components

In embodiments where a lipid nanoparticle comprises three and no more than three distinct components of lipids, the ratio of total lipid content (i.e., the ratio of lipid component (1):lipid component (2):lipid component (3)) can be represented as x:y:z, wherein $(y+z)=100-x$.

In some embodiments, each of "x," "y," and "z" represents molar percentages of the three distinct components of lipids, and the ratio is a molar ratio.

In some embodiments, each of "x," "y," and "z" represents weight percentages of the three distinct components of lipids, and the ratio is a weight ratio.

In some embodiments, lipid component (1), represented by variable "x," is a sterol-based cationic lipid.

In some embodiments, lipid component (2), represented by variable "y," is a helper lipid.

In some embodiments, lipid component (3), represented by variable "z," is a PEG lipid.

In some embodiments, variable "x," representing the molar percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the molar percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the molar percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x" is at least about 50% but less than about 70%; at least about 50% but less than about 65%; or at least about 50% but less than about 60%.

In some embodiments, variable "x," representing the weight percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the weight percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the weight percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x" is at least about 50% but less than about 70%; at least about 50% but less than about 65%; or at least about 50% but less than about 60%.

In some embodiments, variable "z," representing the molar percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z," representing the molar percentage of lipid component (3) (e.g., a PEG lipid) is about 1%, 2%, 3%, 4%, 5%, 6%, 7%, 8%, 9%, 10%. In embodiments, variable "z," representing the molar percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

In some embodiments, variable "z," representing the weight percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z," representing the weight percentage of lipid component (3)

(e.g., a PEG lipid) is about 1%, 2%, 3%, 4%, 5%, 6%, 7%, 8%, 9%, 10%. In embodiments, variable "z," representing the weight percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

For compositions having three and only three distinct lipid components, variables "x," "y," and "z" may be in any combination so long as the total of the three variables sums to 100% of the total lipid content.

Formation of Liposomes Encapsulating mRNA

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (zeta potential), targeting ligands and/or combinations thereof. In some embodiments, the one or more liposome may have a different composition of sterol-based cationic lipids, neutral lipid, PEG-modified lipid and/or combinations thereof. In some embodiments the one or more liposomes may have a different molar ratio of cholesterol-based cationic lipid, neutral lipid, and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating an mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

EXAMPLES

While certain compounds, compositions and methods of the present invention have been described with specificity in accordance with certain embodiments, the following examples serve only to illustrate the compounds of the invention and are not intended to limit the same.

Example 1. Formulation of mRNA-Loaded LNPs for Treatment of Cancer

This example provides exemplary mRNA-loaded lipid nanoparticles (LNPs) used in in vivo efficacy study of treating cancer.

Messenger RNAs encoding codon-optimized, wild-type, or mutated IL-2, IL-12, STING, GM-CSF, FLT-3L, NLRP3, or a combination thereof, as shown in Table 1, were prepared and encapsulated within LNPs comprising cKK-E12. As a negative control, firefly luciferase (FFL) mRNA was encapsulated within LNP.

TABLE 1 mRNA constructs used in in vivo study

| mRNA | Structure | Size (including tail/Cap1) bp | Cap1 (%) |
|---|---|---|---|
| 1 | CO-mscIL-12 | 2284 | — |
| 2 | Chimeric H9 IL-2 | 1054 | 100 |
| 3 | CO-mSTING (R283M) | 1578 | 100 |
| 4 | mGM-CSF | 828 | 100 |
| 5 | CO-mFLT3L | 1142 | 100 |
| 6 | CO-mNLRP3 (D301N) | 4000 | 100 |

*CO: Codon-optimized; msc:mesenchymal stem cells; m: mouse; in parenthesis: mutation

Example 2. Study Design of In Vivo Efficacy of mRNA-LNP in MC38 Mouse Model

This example describes a study design for pre-clinically evaluating the in vivo therapeutic efficacy of mRNA-LNPs in the treatment of the subcutaneous MC38 murine colon cancer syngeneic mouse model.

MC-38 (mouse colorectal cancer cell line) tumors were implanted subcutaneously in immune competent mice. Serum was collected 3-4 days prior to tumor inoculation and at sacrifice. When the implanted tumors grew to a size of 60-80 (mm³) (day 1; d1), mice were injected intratumorally with various mRNA-LNPs prepared as described in Example 1. The injections took six times over the 20 day period at 4-day interval as shown in Table 2. Groups B and C received single agent whereas Groups D-H received a combination of drugs. Group A and I received saline and FFL mRNA-LNP, respectively, as negative controls. Mice were monitored and tumor volume was measured throughout the study until day 46 or until the tumor size exceeded 3000 mm³.

TABLE 2

Study design of MC-38 Colorectal Cancer Mouse Model

| Group | Targets | Number of mice | Dose Amount (µg) | Frequency | Stock |
|---|---|---|---|---|---|
| A | Saline (negative control) | 10 | 0 | d1, d4, d8, d12, d16, d20 | — |
| B | IL-12sc | 10 | 7.5 | d1, d4, d8, d12, d16, d20 | 250 µg/ml |
| C | IL-2† | 10 | 7.5 | d1, d4, d8, d12, d16, d20 | 250 µg/ml |
| D | STING*/IL-12sc | 10 | 7.5 | d1, d4, d8, d12, d16, d20 | 250 µg/ml |
| E | STING*/IL-12sc/GM-CSF | 10 | 7.5 | d1, d4, d8, d12, d16, d20 | 250 µg/ml |
| F | STING*/IL-12sc/FLT-3L/GM-CSF | 10 | 7.5 | d1, d4, d8, d12, d16, d20 | 250 µg/ml |
| G | STING*/IL-12sc/NLRP3#/GM-CSF | 10 | 7.5 | d1, d4, d8, d12, d16, d20 | 250 µg/ml |
| H | STING*/IL-12sc/IL-2†/GM-CSF | 10 | 7.5 | d1, d4, d8, d12, d16, d20 | 250 µg/ml |
| I | FFL (negative control) | 10 | 7.5 | d1, d4, d8, d12, d16, d20 | 250 µg/ml |

*constitutively active;
†chimeric H9;
D301N mutation

Example 3. In Vivo Anti-Tumor Efficacy of mRNA-LNP in MC38 Mouse Model

This example demonstrates an in vivo efficacy of mRNA-LNPs made according to the present invention in decreasing tumor size and inhibiting tumor growth.

Tumor volume was measured at the indicated time points as shown in FIG. 1 and Table 3. Endpoints in the study were either death of the animal or a tumor volume reaching 3000 mm³.

Figure 6:
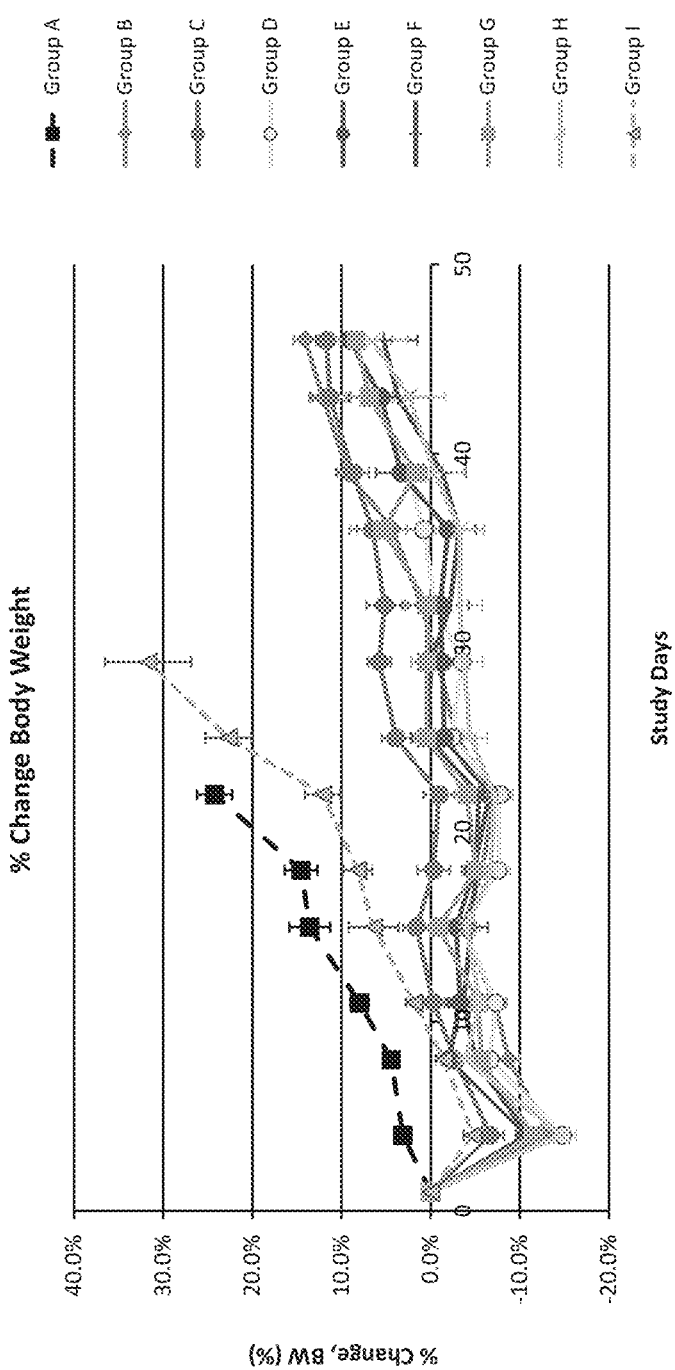
FIG. 6 is a graph depicting mean percent change of body weight throughout the study period as compared to body weight at day 1.

FIG. 1 shows that mean tumor volume of mice in Groups B-H was significantly smaller than that of mice in Groups A or I. Most of the mice in Group A and I died or had tumor volume greater than 3000 mm³ before the study was completed. At the end of the study (d46), complete response (CR) rate was 100% for Group B, 30% Group C, 90% for Group D, 80% for Group E, 90% for Group F, 70% for Group G, and 70% for Group H (See FIG. 5B-5G). Notably, tumor growth was delayed significantly in mice of Group B-H as compared to the negative controls. See Tables 3-6. Additionally, percent change in body weight of Group B-H, as compared to Group A or I, was significantly lower (FIG. 6).

TABLE 3

Mean Tumor Volume (mm3) of each Group measured at different time points

| Day | Group | | | | | | | | |
|---|---|---|---|---|---|---|---|---|---|
| | A | B | C | D | E | F | G | H | I |
| 1 | 68.76 | 68.72 | 68.72 | 68.80 | 68.74 | 68.72 | 68.74 | 68.75 | 68.73 |
| 4 | 149.9 | 146.28 | 187.63 | 153.80 | 177.07 | 145.19 | 160.79 | 165.43 | 160.83 |
| 8 | 448.33 | 203.08 | 257.51 | 197.30 | 214.51 | 186.82 | 208.48 | 225.63 | 301.69 |
| 11 | 752.58 | 214.76 | 304.03 | 222.88 | 239.47 | 217.33 | 252.60 | 251.26 | 384.94 |
| 15 | 1684.07 | 240.17 | 342.13 | 243.75 | 260.22 | 234.69 | 270.32 | 268.23 | 616.28 |
| 18 | 1839.65 | 260.04 | 388.33 | 260.99 | 277.24 | 254.63 | 285.44 | 291.09 | 1000.56 |
| 22 | 3405.32 | 278.20 | 428.29 | 270.65 | 288.31 | 280.27 | 299.24 | 300.27 | 1592.15 |

TABLE 3-continued

Mean Tumor Volume (mm3) of each Group measured at different time points

| Day | A | B | C | D | E | F | G | H | I |
|---|---|---|---|---|---|---|---|---|---|
| 25 | — | 288.30 | 484.10 | 292.17 | 296.94 | 301.04 | 313.14 | 319.13 | 2632.27 |
| 29 | — | 299.96 | 643.20 | 301.42 | 305.93 | 320.11 | 321.49 | 331.63 | 3830.06 |
| 32 | — | 295.75 | 689.31 | 313.28 | 312.87 | 329.47 | 315.87 | 338.34 | — |
| 36 | — | 253.02 | 800.21 | 311.35 | 228.34 | 188.95 | 183.35 | 219.10 | — |
| 39 | — | 142.56 | 663.73 | 368.06 | 180.43 | 156.69 | 162.95 | 160.06 | — |
| 43 | — | 83.82 | 952.53 | 119.75 | 213.11 | 124.22 | 73.88 | 162.78 | — |
| 46 | — | 80.70 | 1332.76 | 75.13 | 28.18 | 143.05 | 34.82 | 154.08 | — |

Figure 2:
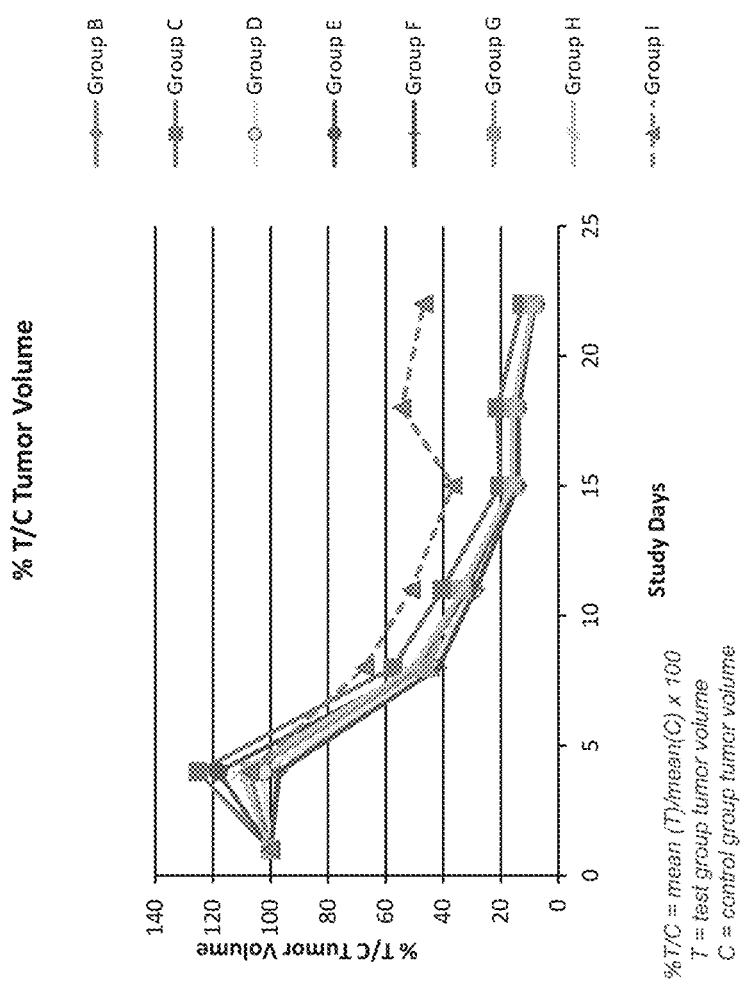
FIG. 2 is a graph depicting mean percent tumor volume of Groups B-I compared to the control group, Group A.
Figure 3:
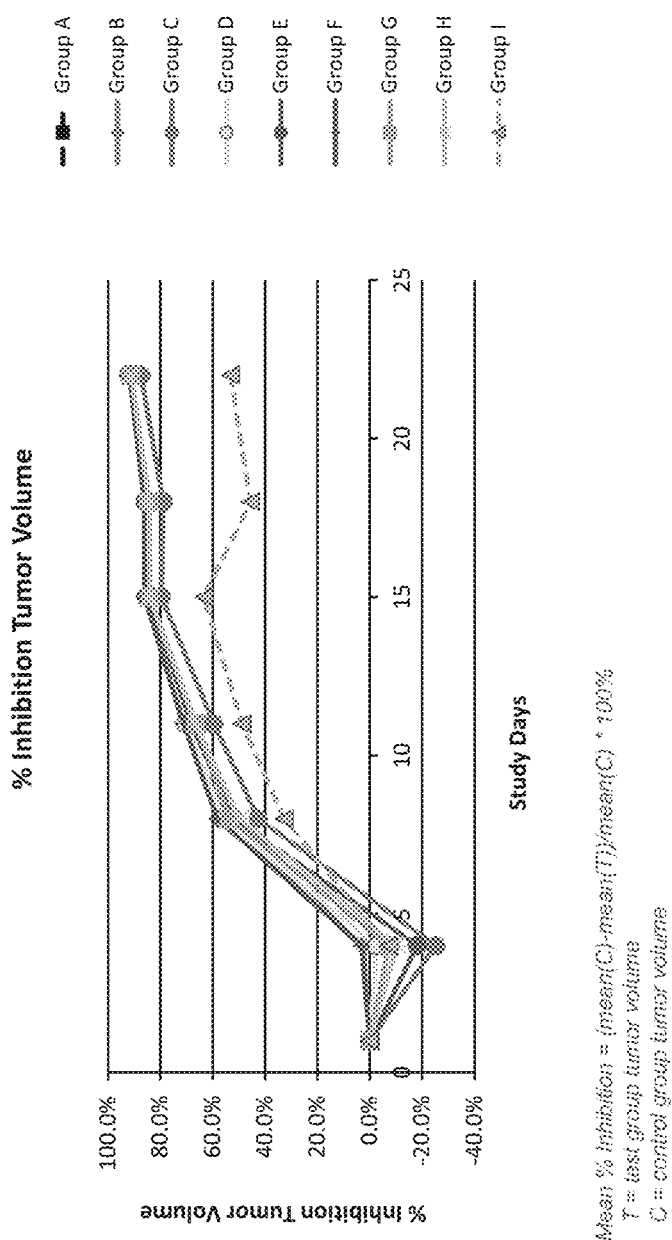
FIG. 3 is a graph depicting mean percent inhibition of tumor volume of Groups B-I compared to the control group, Group A.
Figure 4:
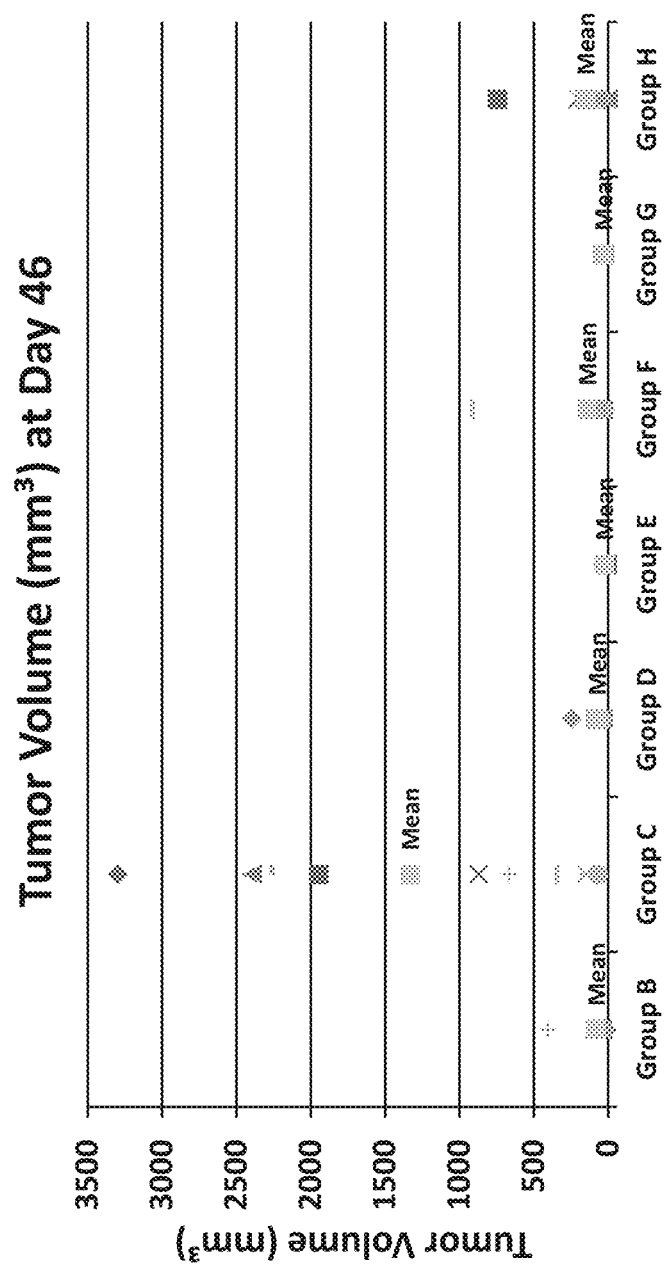
FIG. 4 is a scatter plot depicting tumor volume of individual mouse in each group at Day 46. Mean tumor volume of each group is indicated.

Mean tumor volume in each group was compared to a control group (Group A). Specifically, tumor volume in test group (T) was divided by control group (C) at each time point and its percentage was plotted as shown in FIG. 2. Additionally, % Inhibition of tumor volume was calculated for each group as follows: (mean(C)−mean (T))/mean(C))× 100% and plotted as shown in FIG. 3 and Table 4. Tumor volume of each mouse in Groups B-H as measured at Day 46 was plotted as shown in FIG. 4. A mean value of each group is indicated.

TABLE 4

Mean Percent Inhibition of Tumor Volume (%) of each Group measured at different time points

| Group | 1 | 4 | 8 | 11 | 15 | 18 | 22 |
|---|---|---|---|---|---|---|---|
| B | 0.07 | 2.41 | 54.70 | 71.46 | 85.74 | 85.86 | 91.83 |
| C | 0.06 | −25.17 | 42.56 | 59.60 | 79.68 | 78.89 | 87.42 |
| D | −0.06 | −2.61 | 55.99 | 70.38 | 85.53 | 85.81 | 92.05 |
| E | 0.03 | −18.13 | 52.15 | 68.18 | 84.55 | 84.93 | 91.53 |
| F | 0.06 | 3.14 | 58.33 | 71.12 | 86.06 | 86.16 | 91.77 |
| G | 0.03 | −7.27 | 53.50 | 66.44 | 83.95 | 84.48 | 91.21 |
| H | 0.02 | −10.36 | 49.67 | 66.61 | 84.07 | 84.18 | 91.18 |
| I | 0.05 | −7.30 | 32.71 | 48.85 | 63.41 | 45.61 | 53.25 |

Mean % Inhibition = (mean(C) − mean (T))/mean(C)) * 100%

TABLE 5

% ΔT/ΔC, Tumor Volume of each Group measured at different time points

| Group | 1 | 4 | 8 | 11 | 15 | 18 | 22 |
|---|---|---|---|---|---|---|---|
| B | 100.00 | 95.60 | 35.40 | 21.36 | 10.61 | 10.80 | 6.28 |
| C | 100.00 | 146.56 | 49.74 | 34.41 | 16.93 | 18.05 | 10.78 |
| D | 100.00 | 104.76 | 33.85 | 22.53 | 10.83 | 10.85 | 6.05 |
| E | 100.00 | 133.52 | 38.40 | 24.97 | 11.85 | 11.77 | 6.58 |
| F | 100.00 | 94.24 | 31.11 | 21.73 | 10.27 | 10.50 | 6.34 |
| G | 100.00 | 113.45 | 36.81 | 26.89 | 12.48 | 12.24 | 6.91 |
| H | 100.00 | 119.16 | 41.33 | 26.69 | 12.35 | 12.56 | 6.94 |
| I | 100.00 | 113.53 | 61.38 | 46.24 | 33.90 | 52.62 | 45.66 |

% ΔT/C = (mean (T) − mean (T0))/(mean(C) − mean (C0)) * 100%
T0—test group initial value
C0—control group initial value

TABLE 6

Mean inhibition % ΔT/ΔC, Tumor Volume of each Group measured at different time points

| Group | 4 | 8 | 11 | 15 | 18 | 22 |
|---|---|---|---|---|---|---|
| B | 4.40 | 64.60 | 78.64 | 89.39 | 89.20 | 93.72 |
| C | −46.56 | 50.26 | 65.59 | 83.07 | 81.95 | 89.22 |
| D | −4.76 | 66.15 | 77.47 | 89.17 | 89.15 | 93.95 |
| E | −33.52 | 61.60 | 75.03 | 88.15 | 88.23 | 93.42 |
| F | 5.76 | 68.89 | 78.27 | 89.73 | 89.50 | 93.66 |
| G | −13.45 | 63.19 | 73.11 | 87.52 | 87.76 | 93.09 |
| H | −19.16 | 58.67 | 73.31 | 87.65 | 87.44 | 93.06 |
| I | −13.53 | 38.62 | 53.76 | 66.10 | 47.38 | 54.34 |

Mean % ΔInhibition = ((mean(C) − mean (C0)) − (mean (T) − mean (T0)))/(mean(C) − mean (C0)) * 100%

Overall, this example demonstrates that mRNA-LNPs made according to the present invention were effective for the anti-tumor activity in vivo and treatment for cancer.

μμ

Figure 7:
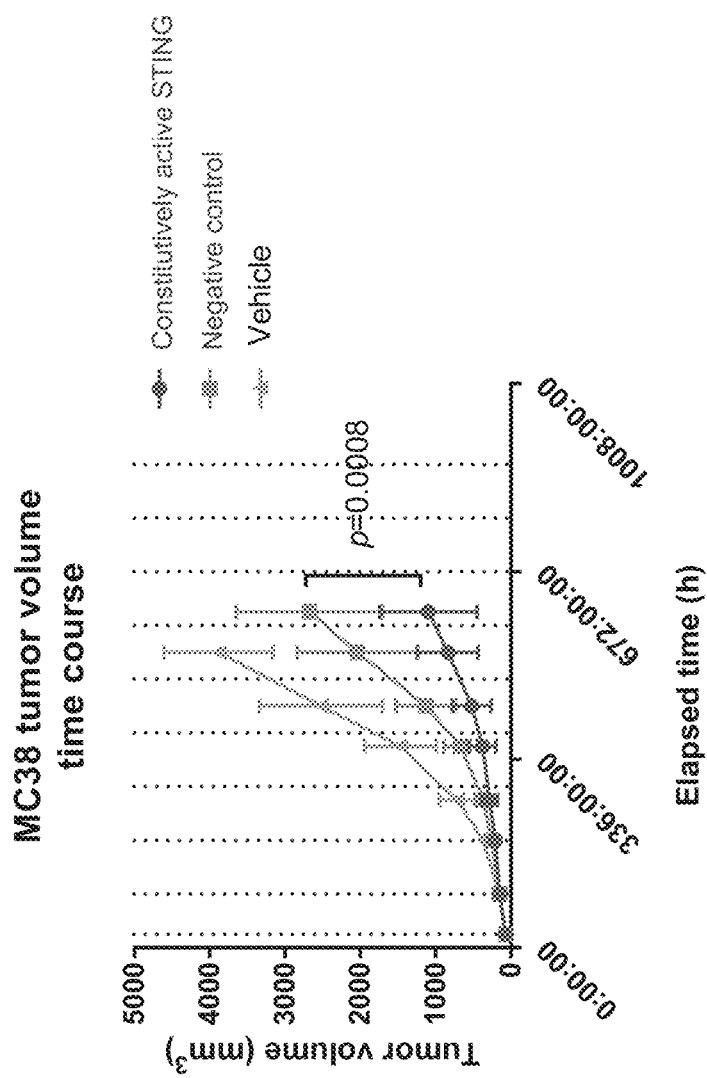
FIG. 7 is a graph that shows tumor growth following administration of lipid-encapsulated, constitutively active STING mRNA, a negative control, or a vehicle control into MC38 mouse cancer model mice.

Example 4. Administration of Lipid Nanoparticle Encapsulated Constitutively Active STING mRNA Delays Tumor Growth and Improves Survival in Animal Models The effect of administering lipid encapsulated, constitutively active STING mRNA on tumor growth and animal was evaluated. For these studies, mouse models (N=10) were inoculated with MC38 tumor cells and the cells were allowed to propagate forming a tumor in the animal model. The animal models were subsequently administered lipid-encapsulated mRNA comprising codon-optimized, constitutively active STING. The lipid nanoparticles were formulated with a cationic lipid of formula I (shown in description above) and 1.5% PEG. The animals received an intratumoral dose every four days of 5 μg of the lipid-encapsulated mRNA. The data from these studies is shown in FIG. 7. As shown in FIG. 7, the animals that received constitutively active STING mRNA had less tumor growth in comparison to a vehicle only control and in comparison to an additional negative control. These data show that administration of lipid encapsulated constitutively active STING results in less tumor growth and a delayed tumor growth profile. These data further show that lipid encapsulated mRNA encoding constitutively active STING is a promising standalone therapeutic for the treatment of cancer.

Figure 8:
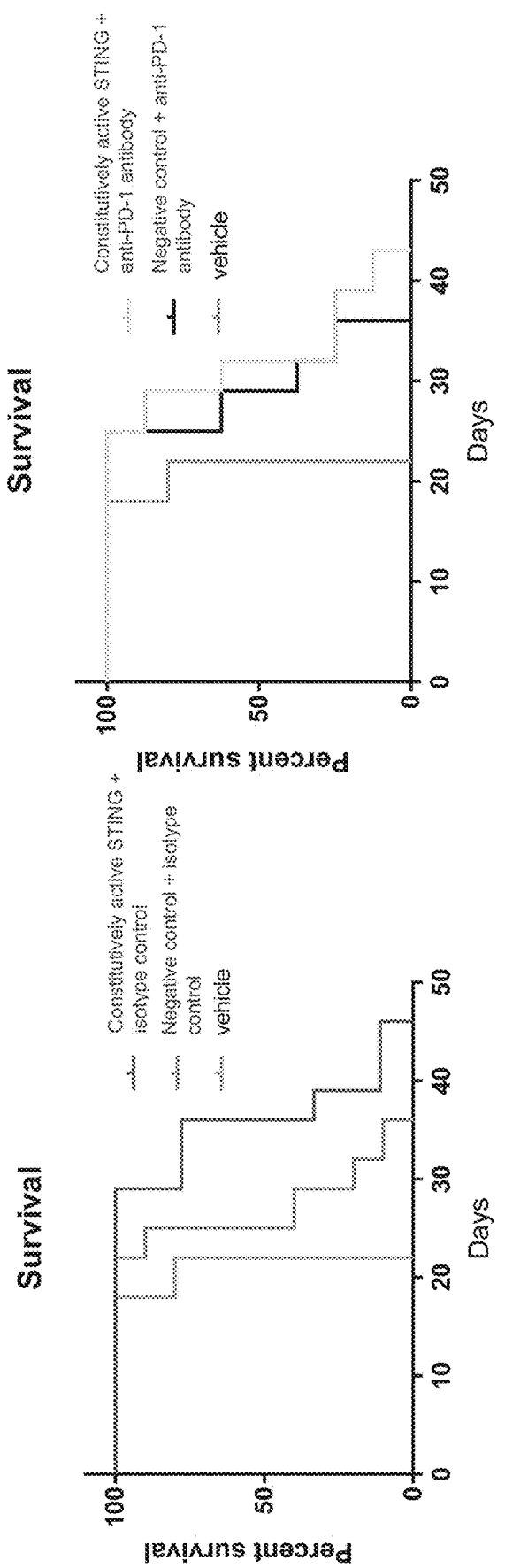
FIG. 8 is a series of graphs that show survival of MC38 cancer mice following administration of 1) lipid-encapsulated, constitutively active STING mRNA and an isotype control antibody; 2) a negative control mRNA and an isotype control antibody; or 3) a vehicle control; in comparison with MC38 cancer mice that were administered: 1) lipid-encapsulated, constitutively active STING mRNA and an anti-PD-1 antibody; 2) a negative control mRNA and an anti-PD-1 antibody; or 3) vehicle control.

Additional studies were performed using the MC38 mouse tumor model described above to assess survival of the animal models following administration of lipid encapsulated, constitutively active STING to the animals. For these studies, the study groups included the following: one group of animals were administered lipid encapsulated, constitutively active STING mRNA, and another group of mice were administered constitutively active STING mRNA in combination with a PD-1 monoclonal antibody. The data from these studies showed that administration of lipid encapsulated, constitutively active STING mRNA improved survival of the animal models without the addition of PD-1 monoclonal antibody (FIG. 8). Taken as a whole, these data show that administration of lipid encapsulated, constitutively active STING mRNA reduces and delays tumor growth, and improves survival.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of treating cancer, comprising administering to a subject in need thereof a composition comprising two or more mRNAs encapsulated within one or more lipid nanoparticle(s), wherein the composition is administered at an effective dose, and an administration interval such that the size of a tumor is reduced or the growth of a tumor is inhibited, wherein two of the two or more mRNAs encode STING and IL-12, respectively, and wherein the one or more lipid nanoparticle(s) each comprise a cationic lipid, a non-cationic lipid, a cholesterol-based lipid, and a PEG-modified lipid.

2. The method of claim 1, wherein the method results in a percent tumor growth inhibition of greater than 50% relative to a control 7 days after administration of an initial dose.

3. The method of claim 1, wherein the lipid nanoparticles further comprise a second lipid nanoparticle comprising a second cationic lipid, wherein the cationic lipid of said one lipid nanoparticle is different from the second cationic lipid.

4. The method of claim 1, wherein the composition is administered intratumorally, subcutaneously, intravenously or intradermally or by pulmonary administration or by nebulization.

5. The method of claim 1, wherein the method comprises injecting a single dose or multiple doses.

6. The method of claim 5, wherein the single dose or the multiple doses range from 0.01 μg mRNA/kg body weight-10 mg mRNA/kg body weight.

7. The method of claim 5, wherein each of the multiple doses comprise the same dosage amount of mRNA or different dosage amounts of mRNA.

8. The method of claim 7, wherein each of the multiple doses are injected 1 day to 3 weeks apart.

9. The method of claim 1, wherein the mRNA comprises one or more modified nucleotides.

10. The method of claim 1, wherein the mRNA comprises a 5' untranslated region (5' UTR) and/or a 3' untranslated region (3' UTR).

11. The method of claim 1, wherein the method further comprises administering to the subject a composition comprising a check point inhibitor.

12. The method of claim 1, wherein the two or more mRNAs comprise at least three mRNAs that encode STING, IL-12 and GM-CSF, respectively.

13. The method of claim 1, wherein the two or more mRNAs comprise at least four mRNAs that encode STING, IL-12, FLT-3L and GM-CSF, respectively.

14. The method of claim 1, wherein the two or more mRNAs comprise at least four mRNAs that encode STING, IL-12, NLRP3 and GM-CSF, respectively.

15. The method of claim 1, wherein the two or more mRNAs comprise at least four mRNAs that encode STING, IL-12, IL-2 and GM-CSF, respectively.

16. The method of claim 1, wherein cationic lipid, non-cationic lipid, cholesterol-based lipid and PEG-modified lipid are present a molar ratio of 30-60:25-35:20-30:1:15.

17. The method of claim 1, wherein the cationic lipid is selected from the group consisting of cKK-E12, OF-00, OF-01, OF-02, and OF-03.

18. The method of claim 1, wherein the STING is a mutant form of the STING which allows the STING to be constitutively active.

* * * * *